(12) United States Patent
Santos et al.

(10) Patent No.: US 9,725,768 B2
(45) Date of Patent: Aug. 8, 2017

(54) METHODS FOR PRODUCING HIGH-FIDELITY AUTOLOGOUS IDIOTYPE VACCINES

(71) Applicant: BIOVEST INTERNATIONAL, INC., Tampa, FL (US)

(72) Inventors: Carlos F. Santos, Minneapolis, MN (US); Amy M. Mccord, New Port Richey, FL (US); Mark Hirschel, Blaine, MN (US)

(73) Assignee: BIOVEST INTERNATIONAL, INC., Tampa, FL (US)

( * ) Notice: Subject to any disclaimer, the term of this patent is extended or adjusted under 35 U.S.C. 154(b) by 171 days.

(21) Appl. No.: 14/424,956

(22) PCT Filed: Aug. 30, 2013

(86) PCT No.: PCT/US2013/057667
§ 371 (c)(1),
(2) Date: Feb. 27, 2015

(87) PCT Pub. No.: WO2014/036488
PCT Pub. Date: Mar. 6, 2014

(65) Prior Publication Data
US 2015/0259749 A1 Sep. 17, 2015

Related U.S. Application Data

(60) Provisional application No. 61/696,053, filed on Aug. 31, 2012.

(51) Int. Cl.
| | |
|---|---|
| C12N 15/00 | (2006.01) |
| C12Q 1/68 | (2006.01) |
| G01N 33/68 | (2006.01) |
| C07K 16/00 | (2006.01) |
| C07K 16/30 | (2006.01) |
| G06F 19/22 | (2011.01) |
| A61K 39/00 | (2006.01) |

(52) U.S. Cl.
CPC ............ C12Q 1/6886 (2013.01); C07K 16/00 (2013.01); C07K 16/30 (2013.01); C12Q 1/6858 (2013.01); G01N 33/686 (2013.01); G06F 19/22 (2013.01); A61K 2039/505 (2013.01); C12Q 2600/156 (2013.01)

(58) Field of Classification Search
None
See application file for complete search history.

(56) References Cited

U.S. PATENT DOCUMENTS

| | | |
|---|---|---|
| 4,971,903 A | 11/1990 | Hyman |
| 4,973,558 A | 11/1990 | Wilson et al. |
| 5,227,159 A | 7/1993 | Miller |
| 5,330,915 A | 7/1994 | Wilson et al. |
| 5,416,022 A | 5/1995 | Amiot |
| 5,541,105 A | 7/1996 | Melink et al. |
| 5,627,070 A | 5/1997 | Gruenberg |
| 5,631,006 A | 5/1997 | Melink et al. |
| 5,656,421 A | 8/1997 | Gebhard et al. |
| 5,861,158 A | 1/1999 | Kwak et al. |
| 5,972,334 A | 10/1999 | Denney, Jr. |
| 5,998,184 A | 12/1999 | Shi |
| 6,001,585 A | 12/1999 | Gramer |
| 6,312,718 B1 | 11/2001 | Popescu et al. |
| 7,208,146 B2 | 4/2007 | Denney, Jr. |
| 7,264,934 B2 | 9/2007 | Fuller |
| 8,383,397 B2 | 2/2013 | Wojciechowski et al. |
| 8,540,499 B2 | 9/2013 | Page et al. |
| 2003/0035807 A1 | 2/2003 | McCormick et al. |
| 2003/0044420 A1 | 3/2003 | McCormick et al. |
| 2003/0082178 A1 | 5/2003 | Gold et al. |
| 2003/0138452 A1 | 7/2003 | Kwak et al. |
| 2005/0095257 A1 | 5/2005 | Kwak et al. |
| 2005/0202004 A1 | 9/2005 | Gold et al. |
| 2005/0238645 A1 | 10/2005 | Gold et al. |
| 2009/0215022 A1 | 8/2009 | Page et al. |
| 2009/0269841 A1 | 10/2009 | Wojciechowski et al. |

(Continued)

FOREIGN PATENT DOCUMENTS

| | | |
|---|---|---|
| EP | 1095948 | 5/2001 |
| WO | WO-94-08601 | 4/1994 |
| WO | WO-98-14170 | 4/1998 |
| WO | WO-2004-052930 | 6/2004 |
| WO | WO-2005-087915 | 9/2005 |
| WO | WO-2005-090403 | 9/2005 |
| WO | WO-2006-084132 | 8/2006 |
| WO | WO-2007-136821 | 11/2007 |
| WO | WO-2007-139742 | 12/2007 |
| WO | WO-2007-139746 | 12/2007 |
| WO | WO-2007-139747 | 12/2007 |
| WO | WO-2007-139748 | 12/2007 |
| WO | WO-2008-034074 | 3/2008 |
| WO | WO-2010-042644 | 4/2010 |
| WO | WO-2010-048417 | 4/2010 |
| WO | WO-2012-021840 | 2/2012 |
| WO | WO-2012-064760 | 5/2012 |
| WO | WO-2012-171026 | 6/2012 |
| WO | WO-2012-171030 | 12/2012 |
| WO | WO-2013-086418 | 12/2012 |
| WO | WO-2014-036488 | 3/2014 |

OTHER PUBLICATIONS

"Errata" *Journal of Clinical Oncology*, Jun. 2000, 18(11):2349-2352.

(Continued)

*Primary Examiner* — Michael Burkhart
(74) *Attorney, Agent, or Firm* — Saliwanchik, Lloyd & Eisenschenk

(57) ABSTRACT

The present invention concerns methods for selecting and producing idiotype vaccines, and in particular methods for selecting and producing an idiotype vaccine for treatment of a B-cell derived malignancy in a subject based on the clonal profile (clonotype) of the malignancy; a method for producing an updated idiotype vaccine matched to a B-cell derived malignancy exhibiting a shifting clonal profile; and the high-fidelity idiotype vaccines produced using the methods. The invention also includes idiotype vaccines produced using the described methods and methods of treating B-cell derived malignancies using the produced vaccines.

26 Claims, 6 Drawing Sheets

(56) References Cited

U.S. PATENT DOCUMENTS

| | | |
|---|---|---|
| 2011/0124111 A1 | 5/2011 | Hoshizaki et al. |
| 2011/0128545 A1 | 6/2011 | Cox et al. |
| 2011/0207135 A1 | 8/2011 | Faham et al. |
| 2012/0114634 A1 | 5/2012 | Stergiou et al. |
| 2012/0208706 A1 | 8/2012 | Downing et al. |
| 2013/0058907 A1 | 3/2013 | Wojciechowski et al. |
| 2014/0037615 A1 | 2/2014 | Santos et al. |
| 2014/0140986 A1 | 5/2014 | Santos et al. |
| 2015/0259749 A1* | 9/2015 | Santos .................. 424/174.1 |

OTHER PUBLICATIONS

Bendandi, M. "Clinical Benefit of Idiotype Vaccines: Too Many Trials for a Clever Demonstration?" *Reviews on Recent Clinical Trials*, 2006, 1(1):67-74.

Bendandi, M. "Idiotype vaccines for lymphoma: proof-of-principles and clinical trial failures" *Nature Reviews*, Sep. 2009, 9:675-681.

Bendandi, M. "Hybridoma-Derived Idiotype Vaccine for Lymphoma: Approval Must Wait" *Pharmaceuticals*, 2010, 3:667-678.

Bendandi, M. et al. "Rapid, high-yield production in plants of individualized idiotype vaccines for non-Hodgkin's lymphoma" *Ann Oncol.*, 2010, 21(12):2420-2427.

Bertinetti, C. et al. "Cloning of idiotype immunoglobulin genes in B cell lymphomas by anchored PCR and production of individual recombinant idiotype vaccines in *Escherichia coli*" *Eur J Haematol*, 2006, 77(5):395-402.

Boyd, S.D. et al. "Measurement and clinical monitoring of human lymphocyte clonality by massively parallel V-D-J pyrosequencing" *Sci Transmed*, 2009, 1(12):1-8.

Campbell, M.J. et al. "Idiotype Vaccination Against Murine B Cell Lymphoma" *The Journal of Immunology*, Oct. 15, 1987, 139(8):2825-2833.

Campbell, P.J. et al. "Subclonal phylogenetic structures in cancer revealed by ultra-deep sequencing" *Proc. Natl. Acad. Sci. U.S.A.*, 2008, 105:13081-13086.

Cavenaugh, J.S. et al. "How Well Can an Idiotope Peptide Mimic Replace Its Parent Idiotype in a Synthetic Peptide Vaccine?" *Pharmaceutical Research*, Aug. 2004, 21(8):1480-1488.

Cheson, B.D. and Leonard, J.P. "Monoclonal antibody therapy for B-cell non-Hodgkin's lymphoma" *N. Engl. J. Med.*, 2008, 359(6):613-626.

Cheson, B.D. et al. "Report of an International Workshop to Standardize Response Criteria for Non-Hodgkin's Lymphomas" *Journal of Clinical Oncology*, Apr. 1999, 17(4):1244-1253.

Cohen, A.D. et al. "Agonist anti-GITR antibody enhances vaccine-induced CD8(+) T-cell responses and tumor immunity" *Cancer Res*, 2006, 66:4904-4912.

De Groot, A.S. et al. "Activation of natural regulatory T cells by IgG Fc-derived peptide 'Tregitopes'" *Blood*, 2008, 112(8):3303-3311.

Dias De Rezende, L.C. et al. "Regulatory T cell as a target for cancer therapy" *Arch. Immunol. Ther. Exp.*, 2010, 58:179-190.

Flowers, C.R. "BiovaxID idiotype vaccination: active immunotherapy for follicular lymphoma" *Expert Review of Vaccines*, Jun. 2007, 6:307-317, Abstract.

Foglietta, M. et al. "Therapeutic Vaccines for Lymphoma: From Bench to Bedside" *American Society of Clinical Oncology*, 2009, pp. 495-500.

Freedman, A. et al. "Placebo-controlled phase III trial of patient-specific immunotherapy with mitumprotimut-T and granulocyte-macrophage colony-stimulating factor after rituximab in patients with follicular lymphoma" *J. Clin. Oncology*, 2009, 27(18):3036-3043.

Galustian, C. et al. "The anti-cancer agents lenalidomide and pomalidomide inhibit proliferation and function of T regulatory cells" *Cancer Immunol Immunother.*, 2009, 58(7):1033-1045.

Gerlinger, M. et al. "Intratumor heterogeneity and branched evolution revealed by multiregion sequencing" *N. Engl. J. Med.*, 2012, 366:883-892.

Ghiringhelli, F. et al. "CD4+CD25+ Regulatory T cells suppress tumor immunity but are sensitive to cyclophosphamide which allows immunotherapy of established tumors to be curative" *Eur. J. Immunol.*, 2004, 34:336-344.

Ghosh, D. "High throughput and global approaches to gene expression" *Comb Chem High Throughput Screen*, 2000, 3:411-420, Abstract.

Hawkins, R. et al. "Idiotypic vaccination against human B-cell lymphoma. Rescue of variable region gene sequences from biopsy material for assembly as single-chain Fv personal vaccines" *Blood*, 1994, 11(11):3279-3888.

Houot, R. et al. "T-cell modulation combined with intratumoral CpG cures lymphoma in a mouse model without the need for chemotherapy" *Blood*, 2009, 113(15):3546-3552.

Hsu, F.J. et al. "Tumor-Specific Idiotype Vaccines in the Treatment of Patients With B-Cell Lymphoma—Long-Term Results of a Clinical Trial" *Blood*, May 1, 1997, 89(9):3129-3135.

Hurvitz, S. A. and Timmerman, J. M. "Recombinant, tumour-derived idiotype vaccination for indolent B cell non-Hodgkin's lymphomas: A focus on FavId™" *Expert Opinion on Biology Therapy* 2005, 5(6): 841-852.

Inogès, S. et al. "Clinical Benefit Associated With Idiotypic Vaccination in Patients With Follicular Lymphoma" *Journal of the National Cancer Institute*, Sep. 20, 2006, 98(18):1292-1301.

Kluskens, L. et al. "Regulation of Immune Response by Autogenous Antibody against Receptor" *Proc. Nat. Acad. Sci. USA*, Dec. 1974, 71(12):5083-5087.

Ko, K. et al. "Treatment of advanced tumors with agonistic anti-GITR mAB and its effects on tumor-infiltrating Foxp3+CD25+CD4+ regulatory T cells" *J. Exp. Med.*, 2005, 202:885-891.

Kwak, L.W. et al. "Combined Syngeneic Bone Marrow Transplantation and Immunotherapy of a Murine B-Cell Lymphoma: Active Immunization With Tumor-Derived Idiotypic Immunoglobulin" *Blood*, Dec. 1, 1990, 76(11):2411-2417.

Kwak, L.W. et al. "Induction of Immune Responses in Patients with B-Cell Lymphoma Against the Surface-Immunoglobulin Idiotype Expressed by their Tumors" *The New England Journal of Medicine*, Oct. 22, 1992, 327(17):1209-1215.

Kwak, L.W. et al. "Active Immunization of Murine Allogeneic Bone Marrow Transplant Donors With B-Cell Tumor—Derived Idiotype: A Strategy for Enhancing the Specific Antitumor Effect of Marrow Grafts" *Blood*, Apr. 1, 1996, 87(7):3053-3060.

Kwak, L.W. et al. "Transfer of myeloma idiotype-specific immunity from an actively immunized marrow donor" *Lancet*, Apr. 22, 1995, 345:1016-1020.

Ladetto, M. et al. "Real-time polymerase chain reaction of immunoglobulin rearrangements for quantitative evaluation of minimal residual disease in multiple myeloma" *Biol. Blood Marrow Transplant.*, 2000, 6:241-253.

Landgren, O. et al. "B-cell clones as early markers for chronic lymphocytic leukemia" *N. Engl. J. Med.*, 2009, 360:659-667.

Lee, S.T. et al. "Therapeutic Vaccine for Lymphoma" *Yonsei Med J*, 2007, 48(1):1-10.

Lee, S.T. et al. "BiovaxID™: a personalized therapeutic cancer vaccine for non-Hodgkin's lymphoma" *Expert Opinion on Biological Therapy*, 2007, 7(1):113-122.

Malyguine, A. et al. "A modified human ELISPOT assay to detect specific responses to primary tumor cell targets" *Journal of Translational Medicine*, Mar. 29, 2004, 2(9):1-11.

Margulies, M. et al. "Genome sequencing in microfabricated high-density picolitre reactors" *Nature*, 2005, 437(7057):376-380.

Min, X.J. and Hickey, D.A. "DNA barcodes provide a quick preview of mitochondrial genome composition" PLoS One, 2007, 2(3):e325 (5 pages).

Navarrete, M et al. "Superior Immunogenicity of Idiotype Fab Fragments as Compared to Entire Immunoglobulin for Active Lymphoma Immunotherapy" *Blood*, 2011, 118:Abst. 1633.

Neelapu, S.S. et al. "Detection of keyhole limpet hemocyanin (KLH)-specific immune responses by intracellular cytokine assay in patients vaccinated with idiotype-KLH vaccine" *J Cancer Res Clin Oncol*, 2001, 127(Suppl 2):R14-R19.

(56) References Cited

OTHER PUBLICATIONS

Neelapu, S.S. et al. "Human Autologous Tumor-Specific T-Cell Responses Induced by Liposomal Delivery of a Lymphoma Antigen" *Clin Cancer Res*, Dec. 15, 2004, 10:8309-8317.

Neelapu, S.S. et al. "Vaccine Therapy for B-Cell Lymphomas: Next-Generation Strategies" *Hematology*, 2007, 243-249.

Neelapu, S.S. et al. "Vaccine-induced tumor-specific immunity despite severe B-cell depletion in mantle cell lymphoma" *Nature Medicine*, Sep. 2005, 11(9):986-991.

Nizar, S. et al. "T-regulatory cell modulation: the future of cancer immunotherapy?" *British Journal of Cancer*, 2009, 100:1697-1703.

Onizuka, S. et al. "Tumor rejection by in vivo administration of anti-CD25 (interleukin-2 receptor alpha) monoclonal antibody" *Cancer Res*, 1999, 59:3128-3133.

Parameswaran, P. et al. "A pyrosequencing-tailored nucleotide barcode design unveils opportunities for large-scale sample multiplexing" *Nucleic Acids Res.*, 2007, 35:e130 (9 pages).

Park, H.J. and Neelapu, S.S. "Developing idiotype vaccines for lymphoma: from preclinical studies to phase III clinical trials" *Br J Haematol.*, 2008, 142:179-191.

Pinna, D. et al. "Clonal dissection of the human memory B-cell repertoire following infection and vaccination" *Eur. J. Immuno.*, 2009, 39:1260-1270.

Rawstron, A.C. et al. "International standardized approach for flow cytometric residual disease monitoring in chronic lymphocytic leukaemia" *Leukemia*, 2007, 21:956-964.

Reitan, S. and Hannestad, K. "Immunoglobulin heavy chain constant regions regulate immunity and tolerance to idiotypes of antibody variable regions" *PNAS*, 2002, 99(11):7588-7593.

Reitan, S. and Hannestad, K. "A syngeneic idiotype is immunogenic when borne by IgM but tolerogenic when joined to IgG" *Eur. J. Immunol.*, 1995, 25:1601-1608.

Rodriguez-Calvillo, M. et al. "Variations in "rescuability" of immunoglobulin molecules from different forms of human lymphoma: implications for anti-idiotype vaccine development" *Crit. Rev. in Oncology/Hematology*, 2004, 52:1-7.

Rosenblatt, J. and Avigan, D. "Cellular immunotherapy for multiple myeloma" *Best Practice & Research Clinical Haematology*, 2008, 21(3):559-577.

Ruffini, P.A., et al. "Idiotypic vaccination for B-cell malignancies as a model for therapeutic cancer vaccines: from prototype protein to second generation vaccines" *Haematologica*, Sep. 2002, 87(9):989-1001.

Sakaguchi, S. "Regulatory T cells: key controllers of immunologic self-tolerance" *Cell*, 2000, 101:455-458.

Sayala, H.A. et al. "Minimal residual disease assessment in chronic lymphocytic leukaemia" *Best Pract. Res. Clin. Haematol.*, 2007, 20:499-512.

Schumacher, K. "Keyhole limpet hemocyanin (KLH) conjugate vaccines as novel therapeutic tools in malignant disorders" *J Cancer Res Clin Oncol*, 2001, 127(Suppl 2):R1-R2.

Shimizu, J. et al. "Induction of tumor immunity by removing CD25+CD4+ T cells: a common basis between tumor immunity and autoimmunity" *J. Immunol.*, 1999, 163:5211-5218.

Sinha, R. et al. "Idiotype vaccine strategies for improving outcomes in follicular lymphoma" *Expert Opinion on Biological Therapy*, 2008; 8(8):1213-1223.

Tanaka, H. et al. "Depletion of CD4+ CD25+ regulatory cells augments the generation of specific immune T cells in tumor-draining lymph nodes" *J. Immunother.*, 2002, 25:207-217.

Tchoudakova, A. et al. "High level expression of functional human IgMs in human PER.C6 cells" *MAbs*, 2009, 1(2):163-171.

Wardemann, H. et al. "B-cell self-tolerance in humans" *Adv. Immunol.*, 2007, 95:83-110, Abstract.

Weng, W.K. et al. "Clinical Outcome of Lymphoma Patients After Idiotype Vaccination is Correlated With Humoral Immune Response and Immunoglobulin G Fc Receptor Genotype" *J Clin Oncol*, Dec. 1, 2004, 22(23):4717-4724.

Wood, C.R. et al. "High level synthesis of immunoglobulins in Chinese hamster ovary cells" *J Immunol*, 1990, 145(9):3011-3016.

* cited by examiner

METHODS FOR PRODUCING HIGH-FIDELITY AUTOLOGOUS IDIOTYPE VACCINES

CROSS-REFERENCE TO RELATED APPLICATIONS

The present application is the National Stage of International Application No. PCT/US2013/057667, filed Aug. 30, 2013, which claims the benefit of U.S. Provisional Application Ser. No. 61/696,053, filed Aug. 31, 2012, each of which is hereby incorporated by reference herein in its entirety, including any figures, tables, nucleic acid sequences, amino acid sequences, or drawings.

BACKGROUND OF INVENTION

The immune system functions as the body's natural defense mechanism for identifying and killing or eliminating disease-causing pathogens, such as bacteria, viruses, or other foreign microorganisms. However, with regard to cancer, including lymphomas, the immune system's natural defense mechanism is believed to be largely thwarted by natural immune system mechanisms which seek to protect "self-cells" from attack. In humans, the primary disease fighting function of the immune system is carried out by white blood cells ("leukocytes"), which mediate two types of immune responses: innate immunity and adaptive immunity. Innate immunity refers to the broad first-line immune defense that recognizes and eliminates certain pathogens prior to the initiation of a more specific adaptive immune response. While the cells of the innate immune system provide a first line of defense, they cannot always eliminate or recognize infectious organisms. In some cases, new infections may not always be recognized or detected by the innate immune system. In these cases, the adaptive immune response has evolved to provide a highly-specific and versatile means of defense which also provides long-lasting protection (immune memory) against subsequent re-infection by the same pathogen. This adaptive immune response facilitates the use of preventative vaccines that protect against viral and bacterial infections such as measles, polio, diphtheria, and tetanus.

Adaptive immunity is mediated by a subset of white blood cells (lymphocytes), which are divided into two types: B-cells and T-cells. In the bloodstream, B-cells and T-cells recognize antigens, which are molecules that are capable of triggering a response in the immune system. The human body makes millions of different types of B-cells that circulate in the blood and lymphatic systems and perform immune surveillance. Each B-cell has a unique receptor protein (immunoglobulin) on its surface that binds to one particular antigen. Once a B-cell recognizes its specific antigen and receives additional signals from a T-helper cell, it can proliferate and become activated in order to secrete antibodies (immunoglobulins; Ig) which can neutralize the antigen and target it for destruction. T-cells may also recognize antigens on foreign cells, whereby they can promote the activation of other white blood cells or initiate destruction of the targeted cells directly. A person's B-cells and T-cells can collectively recognize a wide variety of antigens, but each individual B-cell or T-cell will recognize only one specific antigen. Consequently, in each person's bloodstream, only a relatively few lymphocytes will recognize the same antigen. In this way, the complex repertoire of immune receptors generated by B and T cells enables recognition of diverse threats to the host.

Since B-cell cancers such as non-Hodgkin's lymphoma ("NHL") are tumors arising from a single malignant transformed B-cell, the tumor cells in NHL maintain on their surface the original malignant B-cell's immunoglobulin (collectively referred to as the "tumor idiotype") that is distinct from those found on normal B cells. The tumor idiotype maintained on the surface of each B-cell lymphoma can be used as the tumor-specific antigen for autologous idiotype cancer vaccines.

Since idiotype vaccines are individually manufactured from a tissue biopsy obtained from a patient's own tumor, they are described as personalized vaccines. This approach makes use of the fact that the unique tumor idiotype is expressed exclusively on the cancerous B-cells. So, when a full, high-fidelity copy of the idiotype is used as a vaccine, it can effectively mount a highly-specific anti-lymphoma attack that "trains" the body's own immune system to solely recognize the idiotype as a "foreign invader", thus stimulating and recruiting the patient's own immune system to destroy micro-pockets of cancer cells that may remain following chemotherapy and potentially target and destroy newly arising lymphoma cells, thus delaying or preventing cancer recurrence.

In many cases, including in NHL, cancer cells produce molecules known as tumor-associated antigens, which may or may not be present in normal cells but may be over-produced in cancer cells. T-cells and B-cells have receptors on their surfaces that enable them to recognize the tumor associated antigens. While cancer cells may naturally trigger a B- or T-cell-based immune response during the initial appearance of the disease, this response may be only weakly specific or attenuated in such a way that it does not fully eradicate all tumor cells. Subsequently, tumor cells gradually evolve and escape from this weak immune response and are able to grow into larger tumors. In addition, because cancer cells arise from normal tissue cells, they are often able to exploit or increase existing immune tolerance mechanisms to suppress the body's immune response which would normally destroy them. In other cases, chemotherapy or other treatment regimens used to treat the cancer may themselves weaken the immune response and render it unable to reject and kill tumor cells. Even with an activated immune system; however, the number and size of tumors can often overwhelm the immune system.

B-cell and T-cell antigen receptors with diverse binding activities are generated by genomic rearrangement of variable (V), diversity (D), and joining (J) gene segments separated by highly variable junction regions. Advanced sequencing methods have recently been used to analyze B cell receptor diversity. A recent study using deep sequencing of clonal IgH (Ig heavy chain) receptor genes in chronic lymphocytic leukemia revealed unexpected intraclonal heterogeneity in a subset of cases (Campbell P J et al., "Subclonal phylogenetic structures in cancer revealed by ultra-deep sequencing," *Proc. Natl. Acad. Sci. U.S.A.*, 2008, 105:13081-13086). Time- and labor-intensive multi-parameter flow cytometry or custom-designed patient- and clonal-specific real-time PCR assays have been used for detection of more subtle clonal populations (Sayala H A et al., "Minimal residual disease assessment in chronic lymphocytic leukaemia," *Best Pract. Res. Clin. Haematol.*, 2007, 20:499-512; Ladetto M et al., "Real-time polymerase chain reaction of immunoglobulin rearrangements for quantitative evaluation of minimal residual disease in multiple myeloma, *Biol. Blood Marrow Transplant.*, 2000, 6:241-253; Rawstron A C et al., "International standardized approach for flow cytometric residual disease monitoring in chronic lymphocytic leukaemia," *Leukemia,* 2007, 21:956-964).

Assessment of lymphocyte clonality in human specimens was carried out in a population-based epidemiological study which showed that small amplified B-cell populations can be seen in almost all individuals who go on to develop chronic lymphocytic leukemia (Landgren O et al., "B-cell clones as early markers for chronic lymphocytic leukemia," *N. Engl. J. Med.,* 2009, 360:659-667). Detection and analysis of immune receptor clonality and evolution has been undertaken in normal and pathogenic immune reactions (Pinna D et al., "Clonal dissection of the human memory B-cell repertoire following infection and vaccination," *Eur. J. Immuno.,* 2009, 39:1260-1270; Wardemann H et al., "B-cell self-tolerance in humans," *Adv. Immunol.,* 2007, 95:83-110, each incorporated herein by reference).

Using a bar-coding strategy to achieve pooling of multiple libraries of rearranged IgH V-D-J gene loci from many human blood samples, high-throughput pyrosequencing was performed to characterize the B cell populations in a series of human clinical specimens from cancer patients and healthy people to examine the diversity of their B-cells (Parameswaran P et al., "A pyrosequencing-tailored nucleotide barcode design unveils opportunities for large-scale sample multiplexing," 2007, *Nucleic Acids Res.,* 35:e130, incorporated herein by reference). From healthy individuals, the authors were able to estimate the normal complexity of the B-cell repertoire. With samples from the cancer patients, they obtained disease-specific signatures of clonal B-cell proliferation events. The two distinct V-D-J rearrangements in a lymph node from one cancer patient indicated that there were two separate clonal B-cell populations in the specimen, which was supported by the morphological and immunophenotypic evidence of two different B-cell lymphomas (follicular lymphoma and small lymphocytic lymphoma) in the tissue (Boyd S D et al., "Measurement and clinical monitoring of human lymphocyte clonality by massively parallel V-D-J pyrosequencing," 2009, *Sci Transmed,* 1(12): 1-8, incorporated herein by reference). Intratumor heterogeneity can lead to tumor evolution and adaptation, resulting in underestimation of the tumor genomic complexity. This may pose a major challenge to personalized medicine strategies for B-cell cancers.

BRIEF SUMMARY

The inventors have determined that by analyzing the diversity of idiotypes (the idiotype profile) present in a patient's tumor, it is possible to select idiotype-producing clones for design and production of an idiotype vaccine such that the idiotype profile of the vaccine matches, or is more representative of, the idiotype profile of the patient's tumor, resulting in induction of an immune response that truly targets the patient's particular tumor. Furthermore, clonal signatures of B-cell derived malignancies can be obtained, for example, at the time of disease diagnosis and then monitored on an ongoing basis and used to assess the effects of idiotype vaccines that target these clonal populations, for early detection of disease relapse, and for the production of updated idiotype vaccines that more closely match the tumor's clonal population over time. Since intratumor heterogeneity may foster tumor evolution and adaptation (Gerlinger M. et al., "Intratumor Heterogeneity and Branched Evolution Revealed by Multiregion Sequencing," *N. Engl. J. Med.,* 2012, 366:883-892, incorporated herein by reference), using the method of the invention, the tumor clonal architecture and complexity as it exists at that time may be recapitulated in each prepared idiotype vaccine. Consequently, the clonal fidelity of the prepared idiotype vaccine relative to the malignancy can be maintained, in furtherance of the goal of personalized medicine.

Accordingly, the subject invention provides idiotype vaccines for treatment of a B-cell derived malignancy; methods for selecting an idiotype vaccine for treatment of a B-cell derived malignancy; methods for producing an idiotype vaccine for treatment of a B-cell derived malignancy; and methods for treating a B-cell derived malignancy.

BRIEF DESCRIPTION OF DRAWINGS

(FIG. 2 reproduced from Neelapu et al., *Exp. Opin Biol Ther,* 2007).

As shown in FIG. 3A, advanced stage, previously untreated, follicular lymphoma patients underwent a lymph node biopsy (LN Bx) after enrollment and were treated with prednisone (60 mg/m2 orally daily on days 1 to 14), doxorubicin (25 mg/m2 IV on days 1 and 8), cyclophosphamide (650 mg/m2 IV on days 1 and 8), and etoposide (120 mg/m2 IV on days 1 and 8) (PACE) chemotherapy every 28 days. Patients achieving a complete response (CR)/complete response unconfirmed (CRu) were stratified according to International Prognostic Index (IPI) and number of chemotherapy cycles and randomized 2:1 to receive five injections of the Id-vaccine (Id-KLH+GM-CSF) or control vaccine (KLH+GM-CSF), respectively. As shown in FIG. 3B, two hundred thirty-four patients were enrolled and 117 patients were randomized to receive at least one dose of the blinded vaccine; 76 received Id-vaccine and 41 received control vaccine. Patients receiving fewer than 5 immunizations either withdrew from the study† or relapsed‡ before completion.

DETAILED DISCLOSURE

Figure 1A:
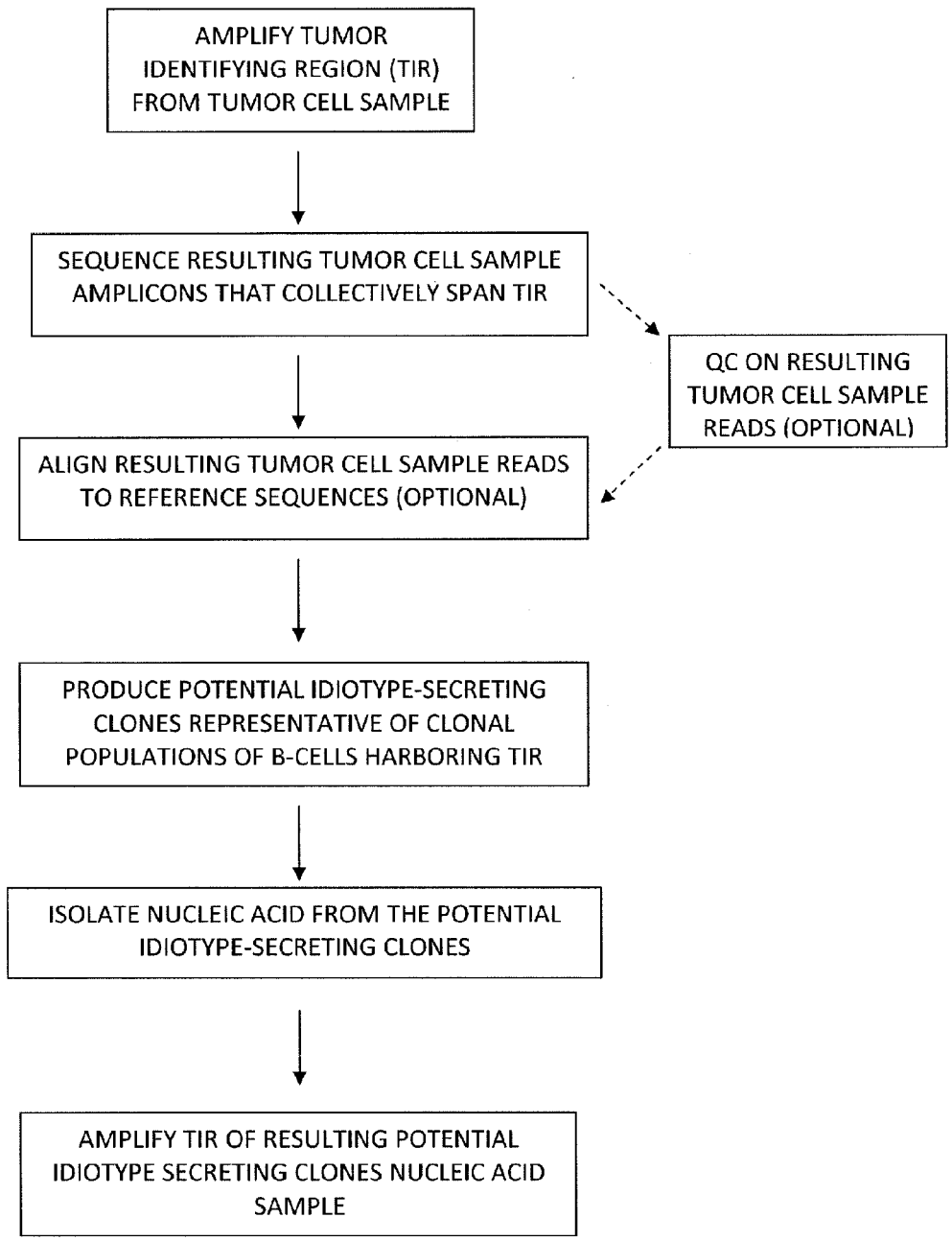
FIGS. 1A and 1B show a flow chart depicting an embodiment of a method of the invention.
Figure 1B:
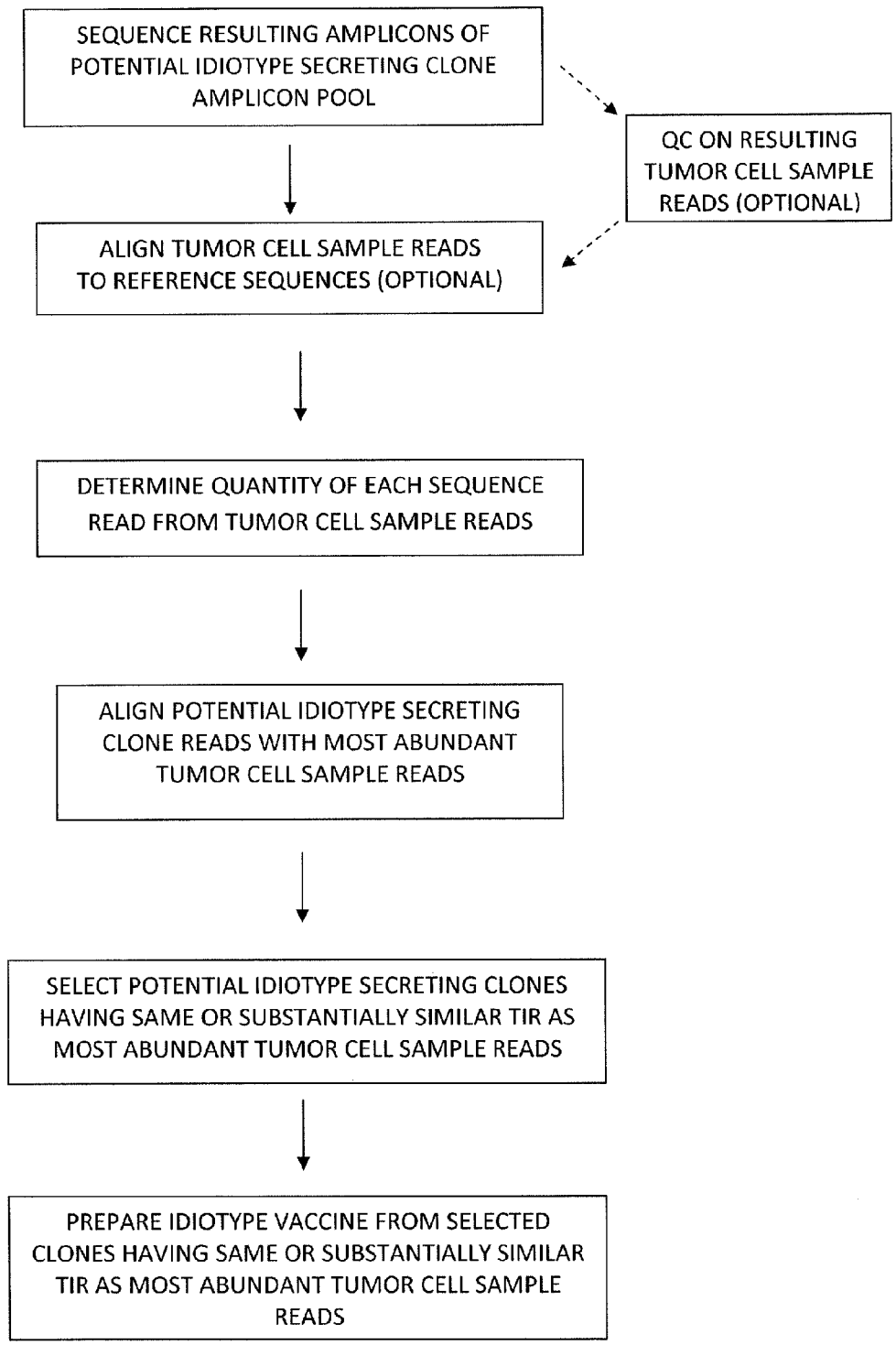

The clonality of expanded B cells can be defined by the analysis of the antigen-binding region (the idiotype, Id) of the immunoglobulin produced and expressed by the B-cell clone. According to the variety of Ids identified, the B-cell derived malignancy may be sustained by monoclonal or polyclonal B-cells. Once the clonal heterogeneity of a B-cell malignancy is analyzed and identified, an idiotype vaccine may be designed based on the selection of those clones that most closely match (most representative of) the clonal profile of the tumor sample, in order to elicit a vaccine-induced immune response against the B-cell clonal profile sustaining the malignancy. How closely a given idiotype vaccine matches the clonal profile of the tumor sample relates to the extent to which the dominant clones of the tumor cell sample are represented within the idiotype vaccine under consideration.

One aspect of the invention concerns a method for producing an idiotype vaccine for treatment of a B-cell derived malignancy in a subject, comprising
  (a) aligning potential idiotype secreting clone reads with tumor cell sample reads that are determined to be the most abundant (the number of unique sequences which comprise e.g., greater than about 10% of the tumor cell sample reads based on sequence similarity clustering), wherein the tumor cell sample reads are sequences of amplicons that collectively span a tumor identifying region, wherein the tumor identifying region comprises a portion of the genomic region of one or more cells of the malignancy that is characteristic of a tumor cell sample of the malignancy, and wherein the potential idiotype secreting clone reads are a quantity of sequences representative of the nucleic acid sequences of the tumor identifying region present in the tumor cell sample of the malignancy;
  (b) selecting one or more potential idiotype secreting clones from the plurality of potential idiotype secreting clones, wherein the selected clone(s) has the same or substantially similar tumor identifying region (e.g., greater than about 80% sequence identity; however, other thresholds may be used) as the most abundant tumor cell sample reads; and
  (c) preparing an idiotype vaccine for treatment of the B-cell derived malignancy, wherein the vaccine comprises an idiotype immunoglobulin from the selected clone(s) having the same or substantially similar tumor identifying region as the most abundant tumor cell sample reads.

In some embodiments, the tumor identifying region of the selected potential idiotype secreting clone(s) has greater than 80%, 81%, 82%, 83%, 84%, 85%, 86%, 87%, 88%, 89%, 90%, 91%, 92%, 93%, 94%, or 95% sequence similarity to the tumor identifying region of the most abundant tumor cell sample reads.

In some embodiments, the tumor cell sample read sequences that are required to cover greater than about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51% or more of the tumor cell sample read sequences comprise the most abundant tumor cell sample read sequences.

Another aspect of the invention concerns a method for selecting an idiotype vaccine for treatment of a B-cell derived malignancy in a subject, comprising:
  (a) sequencing amplicons of a potential idiotype secreting clone amplicon pool, wherein the resulting reads ("potential idiotype secreting clone reads") are a quantity of sequences representative of the nucleic acid sequences of a tumor identifying region present in a cell sample of the malignancy ("tumor cell sample"), wherein the tumor identifying region comprises a portion of the genomic region of one or more cells of the malignancy that is characteristic of the tumor cell sample, and wherein the potential idiotype secreting clone amplicon pool comprises amplicons that collectively span the tumor identifying region;
  (b) aligning tumor cell sample reads to reference sequences, wherein the tumor cell sample reads are sequences of amplicons that collectively span the tumor identifying region;
  (c) determining a quantity of each sequence read from the tumor cell sample reads;
  (d) aligning the potential idiotype secreting clone reads with the most abundant tumor cell sample reads (the number of unique sequences which comprise e.g., greater than about 10% of the tumor cell sample reads based on sequence similarity clustering); and
  (e) selecting one or more potential idiotype secreting clones from the plurality of potential idiotype secreting clones, wherein the selected clone(s) has the same or substantially similar tumor identifying region (e.g., greater than about 80% sequence identity; however, other thresholds may be used) as the most abundant tumor cell sample reads.

In some embodiments, the tumor identifying region of the selected potential idiotype secreting clone(s) has greater than 80%, 81%, 82%, 83%, 84%, 85%, 86%, 87%, 88%, 89%, 90%, 91%, 92%, 93%, 94%, or 95% sequence similarity to the tumor identifying region of the most abundant tumor cell sample reads.

In some embodiments, the tumor cell sample read sequences that are required to cover greater than about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51% or more of the tumor cell sample read sequences comprise the most abundant tumor cell sample read sequences.

In some embodiments, the method further comprises: (f) preparing an idiotype vaccine for treatment of the B-cell derived malignancy, wherein the vaccine comprises an idiotype immunoglobulin from the selected clone(s) having the same or substantially similar tumor identifying region as the most abundant tumor cell sample reads. Optionally, the method further comprises: (g) administering the idiotype vaccine to the subject.

In some embodiments, the method for selecting an idiotype vaccine for treatment of a B-cell derived malignancy in a subject comprises:
  (a) sequencing amplicons that collectively span a portion of the genomic region of one or more cells that is characteristic of a B-cell malignancy tumor cell sample (the "tumor identifying region"), resulting in reads (the "tumor cell sample reads") that are a quantity of sequences representative of the nucleic acid sequences of the tumor identifying region present in the tumor cell sample;

(b) aligning the tumor cell sample reads to reference sequences;
(c) producing a plurality of clones from the tumor cell sample ("potential idiotype-secreting clones"), wherein each clone is representative of one clonal population of B-cells harboring the tumor identifying region common to one clonal population of B-cells;
(d) isolating nucleic acid from one or more of the potential idiotype-secreting clones ("potential idiotype secreting clones nucleic acid sample");
(e) amplifying at least a portion of the tumor identifying region of the potential idiotype secreting clones nucleic acid sample, resulting in amplicons that collectively span the tumor identifying region ("the potential idiotype secreting clone amplicon pool");
(f) sequencing the amplicons of the potential idiotype secreting clone amplicon pool, wherein the resulting reads ("potential idiotype secreting clone reads") are a quantity of sequences representative of the nucleic acid sequences of the tumor identifying region present in the tumor cell sample;
(g) aligning the tumor cell sample reads to reference sequences;
(h) determining a quantity of each sequence read from the tumor cell sample reads;
(i) aligning the potential idiotype secreting clone reads with the most abundant tumor cell sample reads (the number of unique sequences which comprise e.g., greater than about 10% of the tumor cell sample reads based on sequence similarity clustering); and
(j) selecting one or more potential idiotype secreting clones from the plurality of potential idiotype secreting clones, wherein the selected clone(s) has the same or substantially similar tumor identifying region (e.g., greater than about 80% sequence identity; however, other thresholds may be used) as the most abundant tumor cell sample reads.

In some embodiments, the tumor identifying region of the selected potential idiotype secreting clone(s) has greater than 80%, 81%, 82%, 83%, 84%, 85%, 86%, 87%, 88%, 89%, 90%, 91%, 92%, 93%, 94%, or 95% sequence similarity to the tumor identifying region of the most abundant tumor cell sample reads.

In some embodiments, the method further comprising: (k) preparing an idiotype vaccine for treatment of the B-cell derived malignancy, wherein the vaccine comprises an idiotype immunoglobulin from the selected clone(s) having the same or substantially similar tumor identifying region as the most abundant tumor cell sample reads. Optionally, the method further comprises: (l) administering the idiotype vaccine to the subject.

In some embodiments, the method for selecting an idiotype vaccine for treatment of a B-cell derived malignancy in a subject, comprising:
(a) obtaining isolated nucleic acid from a cell sample comprising one or more cells of the B-cell derived malignancy (the "tumor cell sample");
(b) amplifying at least a portion of the genomic region of the one or more cells that is characteristic of the tumor cell sample (the "tumor identifying region"), resulting in amplicons that collectively span the tumor identifying region (the "tumor cell sample amplicons");
(c) sequencing the tumor cell sample amplicons, resulting in reads (the "tumor cell sample reads") that are a quantity of sequences representative of the nucleic acid sequences of the tumor identifying region present in the tumor cell sample;
(d) aligning the tumor cell sample reads to reference sequences;
(e) producing a plurality of clones from the tumor cell sample ("potential idiotype-secreting clones"), wherein each clone is representative of one clonal population of B-cells harboring the tumor identifying region common to one clonal population of B-cells;
(f) isolating nucleic acid from one or more of the potential idiotype-secreting clones ("potential idiotype secreting clones nucleic acid sample");
(g) amplifying at least a portion of the tumor identifying region of the potential idiotype secreting clones nucleic acid sample, resulting in amplicons that collectively span the tumor identifying region ("the potential idiotype secreting clone amplicon pool");
(h) sequencing the amplicons of the potential idiotype secreting clone amplicon pool, wherein the resulting reads ("potential idiotype secreting clone reads") are a quantity of sequences representative of the nucleic acid sequences of the tumor identifying region present in the tumor cell sample;
(i) aligning the tumor cell sample reads to reference sequences;
(j) determining a quantity of each sequence read from the tumor cell sample reads;
(k) aligning the potential idiotype secreting clone reads with the most abundant tumor cell sample reads (the number of unique sequences which comprise e.g., greater than about 10% of the tumor cell sample reads based on sequence similarity clustering); and
(l) selecting one or more potential idiotype secreting clones from the plurality of potential idiotype secreting clones, wherein the selected clone(s) has the same or substantially similar tumor identifying region (e.g., greater than about 80% sequence identity; however, other thresholds may be used) as the most abundant tumor cell sample reads.

In some embodiments, the tumor identifying region of the selected potential idiotype secreting clone(s) has greater than 80%, 81%, 82%, 83%, 84%, 85%, 86%, 87%, 88%, 89%, 90%, 91%, 92%, 93%, 94%, or 95% sequence similarity to the tumor identifying region of the most abundant tumor cell sample reads.

Optionally, the method further includes: (m) preparing an idiotype vaccine for treatment of the B-cell derived malignancy, wherein the vaccine comprises an idiotype immunoglobulin from the selected clone(s) having the same or substantially similar tumor identifying region as the most abundant tumor cell sample reads.

The invention includes the idiotype vaccines prepared using any methods of the invention described herein, including the first-generation vaccines (vaccines initially prepared for the subjects) and next-generation vaccines (updated vaccines), which may be used for treatment of a B-cell derived malignancy. The invention further includes methods of treating a B-cell derived malignancy in a subject comprising administering an effective amount of an idiotype vaccine selected and produced using the methods of the invention.

Optionally, the method includes a treatment step comprising administering the prepared idiotype vaccine to the subject. The idiotype vaccine may be administered with or without an adjuvant. Adjuvants are nonspecific stimulators of the immune response. When mixed with an antigen or immunogen, adjuvants help to deposit or sequester the injected material thereby helping to increase antibody response. Adjuvants enhance the immune response to compounds that are already immunogenic, as opposed to conferring immunogenicity to non-immunogenic haptens. To make prospective antigens more immunogenic, they may be conjugated to a carrier protein or some other complex, immunogenic molecule. (Freund, J., "The mode of action of immunologic adjuvants", *Adv. Tuberc. Res.* 1956, 7:130-148; Harlow, E. and Lane, D. Antibodies: A Laboratory Manual, 1988, Cold Spring Harbor, N.Y.: Cold Spring Harbor Laboratory, pp. 56-100). Preferably, the method further comprises administering granulocyte monocyte-colony stimulating factor (GM-CSF) or another adjuvant. Examples of other adjuvants include Freund's complete adjuvant (FCA) and Freund's incomplete adjuvant (FIA).

Optionally, the idiotype immunoglobulin may be conjugated to an immunogenic carrier molecule, such as keyhole limpet hemocyanin (KLH). Many proteins can be used as carrier molecules and are chosen based on immunogenicity, solubility, and availability of useful functional groups through which conjugation can be achieved. Other examples of carrier molecules that may be conjugated include, but are not limited to, cationized or non-cationized bovine serum albumin (BSA), ovalbumin (OVA), and Blue Carrier Protein (a purified preparation of *Concholepas choncholepas* hemocyanin (CCH)). Preparing the idiotype vaccine can include a step of conjugating the idiotype immunoglobulin with the immunogenic carrier molecule.

Several approaches are available for conjugating carrier proteins to selected idiotype immunoglobulins, such as EDC conjugation, maleimide conjugation, glutaraldehyde conjugation). The choice of which conjugation chemistry to use depends on the functional groups available, the required immunoglobulin orientation and distance from the carrier, and the possible effect of conjugation on biological and antigenic properties. For example, proteins and peptides have primary amines (the N-terminus and the side chain of lysine residues), carboxylic groups (C-terminus or the side chain of aspartic acid and glutamic acid), and sulfhydryls (side chain of cysteine residues) that can be targeted for conjugation. Generally, it is the many primary amines in a carrier protein that are used to couple the immunoglobulin via a crosslinking reagent.

Optionally, the B-cell derived malignancy is in complete remission at the time the idiotype vaccine is administered to the subject. The malignancy may be placed in complete remission, for example, by surgery, chemotherapy, immunotherapy, or a combination of two or more of the foregoing.

The tumor cell sample may be a sample of blood, bone marrow, or lymph node. The method of the invention may include a step of isolating the nucleic acid from the tumor cell sample prior to step (a). The isolated nucleic acid of the tumor cell sample may be genomic DNA or RNA. The sample may be obtained from a single region of the tumor or multiple regions of the tumor (a multi-region sample).

Step (k) of the method involves aligning the potential idiotype secreting clone reads with the most abundant tumor cell sample reads (e.g., the number of unique sequences which comprise greater than about 10% of the tumor cell sample reads based on sequence similarity clustering). In some embodiments, the tumor cell sample read sequences that are required to cover greater than about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51% or more of the tumor cell sample read sequences comprise the most abundant tumor cell sample read sequences. U.S. Patent Publication No. 20110207135 (Faham M. et al.; assigned to Sequenta, Inc.), entitled "Methods of Monitoring Conditions by Sequence Analysis" (incorporated herein by reference) describes a method for determining a clonotype profile of T cell receptors and/or B cell receptors of an individual comprising the following steps: (a) obtaining a nucleic acid sample from T-cells and/or B-cells of the individual; (b) spatially isolating individual molecules derived from such nucleic acid sample, the individual molecules comprising nested sets of templates each generated from a nucleic acid in the sample and each containing a somatically rearranged region or a portion thereof, each nested set being capable of producing a plurality of sequence reads each extending in the same direction and each starting from a different position on the nucleic acid from which the nested set was generated; (c) sequencing said spatially isolated individual molecules; and (d) determining abundances of different sequences of the nucleic acid molecules from the nucleic acid sample to generate the clonotype profile. The method in U.S. Patent Publication No. 20110207135 may be used to determine relative abundances of the tumor cell sample reads, particularly to generate a "clonotype" for IgH molecules with only a small (~100 bp) read.

In some embodiments, the tumor identifying region of step (b) comprises complementarity determining region 3 (CDR3) of the immunoglobulin heavy chain (IgH) gene.

In some embodiments, the tumor identifying region of step (b) comprises:
(a) a rearranged VDJ region of the immunoglobulin heavy chain (IgH) gene; or
(b) a rearranged VJ region of the immunoglobulin kappa (IgK) gene; or
(c) a rearranged VJ region of the immunoglobulin lambda (IgL) gene.

In some embodiments, the tumor identifying region of step (b) is a translocation region associated with the B-cell derived malignancy, such as:
(a) a bcl-1/IgH fusion sequence, wherein the B-cell derived malignancy is mantle cell lymphoma (MCL); or
(b) a bcl-2/IgH fusion sequence, wherein the B-cell derived malignancy is follicular lymphoma; or
(c) a bcl-3/IgH fusion sequence, wherein the B-cell derived malignancy is B-cell chronic lymphocytic leukemia (CLL); or
(d) a bcl-6/IgH fusion sequence, wherein the B-cell derived malignancy is diffuse large cell lymphoma (DLCL); or
(e) a fibroblast growth factor receptor (FGFR)/IgH fusion sequence, wherein the B-cell derived malignancy is multiple myeloma; or
(f) a cyclin D1 sequence, wherein the B-cell derived malignancy is multiple myeloma; or
(g) a c-myc/IgH fusion sequence, wherein the B-cell derived malignancy is Burkitt's lymphoma; or
(h) a bcl-6/IgL fusion sequence, wherein the B-cell derived malignancy is diffuse large cell lymphoma (DLCL); or
(i) a bcl-6 or CD95 (a.k.a. FAS or APO1) fusion sequence; wherein the B-cell derived malignancy is Non-Hodgkin's lymphoma (NHL); or
(j) a Pax-5, c-myc, Pim-1, or Rho/TTF sequence; wherein the B-cell derived malignancy is DLCL; or
(k) a bcl-6, Pax-5, c-myc, Pim-1, Rho/TTF sequence; wherein the B-cell derived malignancy is NHL.

In some embodiments, the tumor identifying region comprises a unique genetic element, such as a translocation, single nucleotide polymorphism (SNP), or somatic mutation.

Optionally, the method further comprises sequencing the nucleic acid of the tumor sample entirely using whole genome sequencing or exome sequencing; and aligning the determined nucleic acid sequences with reference sequences to identify the unique genetic elements of the one or more cells of the tumor cell sample. Vast repositories of known biological sequences are often contained in shared computing resources.

As used herein, "aligning" means a comparison involving performing a similarity search of a query sequence against a database of sequence records using any one of a large number of algorithms for determining similarity. Sequences that are said to be "comparable" have a sufficient degree of similarity to at least one sequence in a database to result in the return of at least one statistically significant (user defined) result. It is straightforward for an end user to visually identify and select contiguous stretches of nucleotide base calls (comprised of only A, T, C, or G residues) or amino acids that might be comparable. Similarity search algorithms include, but are not limited to, commonly used local alignment (e.g., Smith-Waterman, BLASTN) sequence alignment algorithms to statistically determine the probability that a given target sequence corresponds to a specific sequence in a database record. The most prevalent comparison method, or similarity search algorithm, for sequence data currently in use is the National Center for Biotechnology Information's (NCBIs) Basic Local Alignment Search Tool, commonly known as and referred to herein as "BLAST." Numerous variants exist, including Washington University BLAST (WU-BLAST), NCBI-BLAST, FASTA, MPsrch, Scanps, and BestFit. Such comparisons generally yield a number of possible matches in terms of certainty (measured probabilistically) that the tested sample includes the matched biological subject for which a sequence is known. Sequence alignment algorithms that are particularly useful in the context of the invention include CD-HIT (http://weizhong-lab.ucsd.edu/cd-hit/), SSAHA2 (http://www.sanger.ac.uk/resources/software/ssaha/), immunoglobulin BLAST (IgBLAST), the International ImMunoGene Tics (IMGT) database, and the iHMMune-align alignment tool.

As indicated above, sequence identity between nucleotide or amino acid sequences can be determined by comparing an alignment of the sequences. When an equivalent position in the compared sequences is occupied by the same amino acid or base, then the molecules are identical at that position. Scoring an alignment as a percentage of identity is a function of the number of identical amino acids or bases at positions shared by the compared sequences. When comparing sequences, optimal alignments may require gaps to be introduced into one or more of the sequences to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties.

Suitable computer algorithms for carrying out sequence comparisons are widely available in the commercial and public sector. Examples include MatGat (Campanella et al., 2003, BMC Bioinformatics 4: 29; program available from http://bitincka.com/ledion/matgat), Gap (Needleman & Wunsch, 1970, J. Mol. Biol. 48: 443-453), FASTA (Altschul et al., 1990, J. Mol: Biol. 215: 403-410; program available from http://www.ebi.ac.uk/fasta), Clustal W 2.0 and X 2.0 (Larkin et al., 2007, Bioinformatics 23: 2947-2948; program available from http://www.ebi.ac.uk/tools/clustalw2) and EMBOSS Pairwise Alignment Algorithms (Needleman & Wunsch, 1970, supra; Kruskal, 1983, In: Time warps, string edits and macromolecules: the theory and practice of sequence comparison, Sankoff & Kruskal (eds), pp. 1-44, Addison Wesley; programs available from http://www.ebi.ac.uk/tools/emboss/align). All programs may be run using default parameters.

For example, sequence comparisons may be undertaken using the "needle" method of the EMBOSS Pairwise Alignment Algorithms, which determines an optimum alignment (including gaps) of two sequences when considered over their entire length and provides a percentage identity score. Default parameters for amino acid sequence comparisons ("Protein Molecule" option) may be Gap Extend penalty: 0.5, Gap Open penalty: 10.0, Matrix: Blosum 62. Default parameters for nucleotide sequence comparisons ("DNA Molecule" option) may be Gap Extend penalty: 0.5, Gap Open penalty: 10.0, Matrix: DNAfull. (e.g., using the National Center for Biotechnology Information's (NCBI's) Basic Local Alignment Search Tool (BLAST), immunoglobulin BLAST (IgBLAST), the International ImMunoGene Tics (IMGT) database, iHMMune-align alignment tool).

In some embodiments, the tumor cell sample amplicons are aligned to reference sequences using a Smith-Waterman algorithm (Waterman, M. S. Introduction to Computational Biology: Maps, sequences and genomes, Chapman & Hall. London (1995)) or a hidden Markov-based alignment.

As a specific example of use of an alignment algorithm, the following steps may be carried out:

1) Split samples in FASTA format into representative patient tumor and hybridoma groups;

1.5) Do quality control using R (ShortRead package): filter out base calls with a PHRED score <20 and replacing them with "N's", and optionally filtering out sequences shorter than the appropriate VDJ read length (so filter out sequences <200 bp and >400 bp), or sequences of low quality (mean PHRED score <30);

2) For each tumor sequence batch, perform a clustering using CD-HIT-454 (e.g., 80% sequence identity to cluster), this reduces the population to a manageable size, and gives us single sequences to align tumor vs hybridoma;

3) For each biopsy sequence batch, perform a clustering using CD-HIT-454 (e.g., 80% sequence identity to cluster) as we did with the tumor sequences;

4) Align each representative cluster sequence in the biopsy against the representative cluster sequence in the hybridoma using the SSAHA2 package www.sanger.ac.uk/resources/software/ssaha2/;

5) Filter the SSAHA2 alignments to throw out poor alignments between tumor and hybridoma clusters (say, alignments containing less than 150 identical bases);

6) Compute similarity between tumor and hybridoma by comparing the size of matched clusters (this gives you a proxy for relative abundance of cells bearing the VDJ region) and then determining whether or not the sequences in the hybridoma really reflect the sequences in the tumor; and 7) The final diagram can be visualized by a Ruby script that plots this as a plot in Cytoscape, or more conveniently, by an algorithm that determines which clusters are largest and computes the degree of matching between the particular hybridoma and the tumor (e.g. 15% of the hybridoma matches 10% of the biopsy VDJ sequences).

Optionally, iHMMune-align (www.emi.unsw.edu.au/~ihmmune/index.php) can be used to call V-D-J genes in either sample, and match based on called sequences; however, this is more complicated in the many cases where the package cannot determine a true VDJ boundary, and so it leads to a significant amount of discarded sequences.

Optionally, in (k) of the method, when aligning the potential idiotype secreting clone reads with the most abundant tumor cell sample reads, the tumor cell sample reads can be ranked and/or visualized on the basis of the extent of each unique sequence's abundance. Software has been used in the past for the visualization of complex biological networks, such as genetic networks and metabolic pathways, and is now increasingly applied in protein interaction networks, such as Cytoscape (www.cytoscape.org), visANT's Integrative Visual Analysis Tool for Biological Networks and Pathways and the Ontario Cancer Institute's NAViGaTOR (Network Analysis, Visualization, & Graphing TORonto) software. Such protein-protein network plotting software may be used to rank and visualize the extent of each unique sequence's abundance.

In some embodiments, the tumor identifying region of step (b) comprises a rearranged VDJ region of the immunoglobulin heavy chain (IgH) gene, and wherein said amplifying of step (b) comprises amplifying DNA between primers that target the framework region (FR1, FR2, and/or FR3) and joining (J) region of the IgH variable gene of the one or more cells. For example, the amplifying of step (b) may be carried out using 7 forward primers for the FR2 region (to account for the 7 common family members of the FR2 region) and 1 consensus primer for the IgH J segment.

In some embodiments, the sequencing step of (c) comprises high-throughput sequencing (HTS), such as pyrosequencing, semiconductor sequencing, or sequencing by synthesis (SBS). In some embodiments, the HTS generates a target of at least 15,000 reads per sample.

In some embodiments, the tumor identifying region of step (b) comprises a rearranged VDJ region of the immunoglobulin heavy chain (IgH) gene, and the tumor cell sample reads are a quantity of sequences representative of the nucleic acid sequences of the VDJ region present in the tumor cell sample.

In some embodiments, the reference sequences of (d) are sequences in one or more publicly available databases (e.g., using the National Center for Biotechnology Information's (NCBI's) Basic Local Alignment Search Tool (BLAST)).

In some embodiments, the tumor identifying region of (b) comprises a rearranged VDJ region of the immunoglobulin heavy chain (IgH) gene, and wherein said aligning of (d) further comprises assigning a V, D, and J allele to tumor cell sample amplicons by aligning the tumor cell sample amplicons with nucleotide sequences from publicly available databases (e.g., using the National Center for Biotechnology Information's (NCBI's) Basic Local Alignment Search Tool (BLAST), immunoglobulin BLAST (IgBLAST), the International ImMunoGene Tics (IMGT) database, iHMMune-align alignment tool).

In some embodiments, the tumor cell sample amplicons are aligned to reference sequences using a Smith-Waterman algorithm or a hidden Markov-based alignment.

Optionally, the method further comprises performing a quality control step on the tumor cell sample reads of (c). In some embodiments, the quality control step comprises: eliminating any tumor cell sample reads of (c) that are the result of sequence artifact; and/or assigning a quality score to each tumor cell sample read of (c), comparing each assigned quality score to a reference threshold quality score, and replacing or annotating any nucleotides in each tumor cell sample amplicon designated not to have achieved the threshold quality score.

Figure 2:
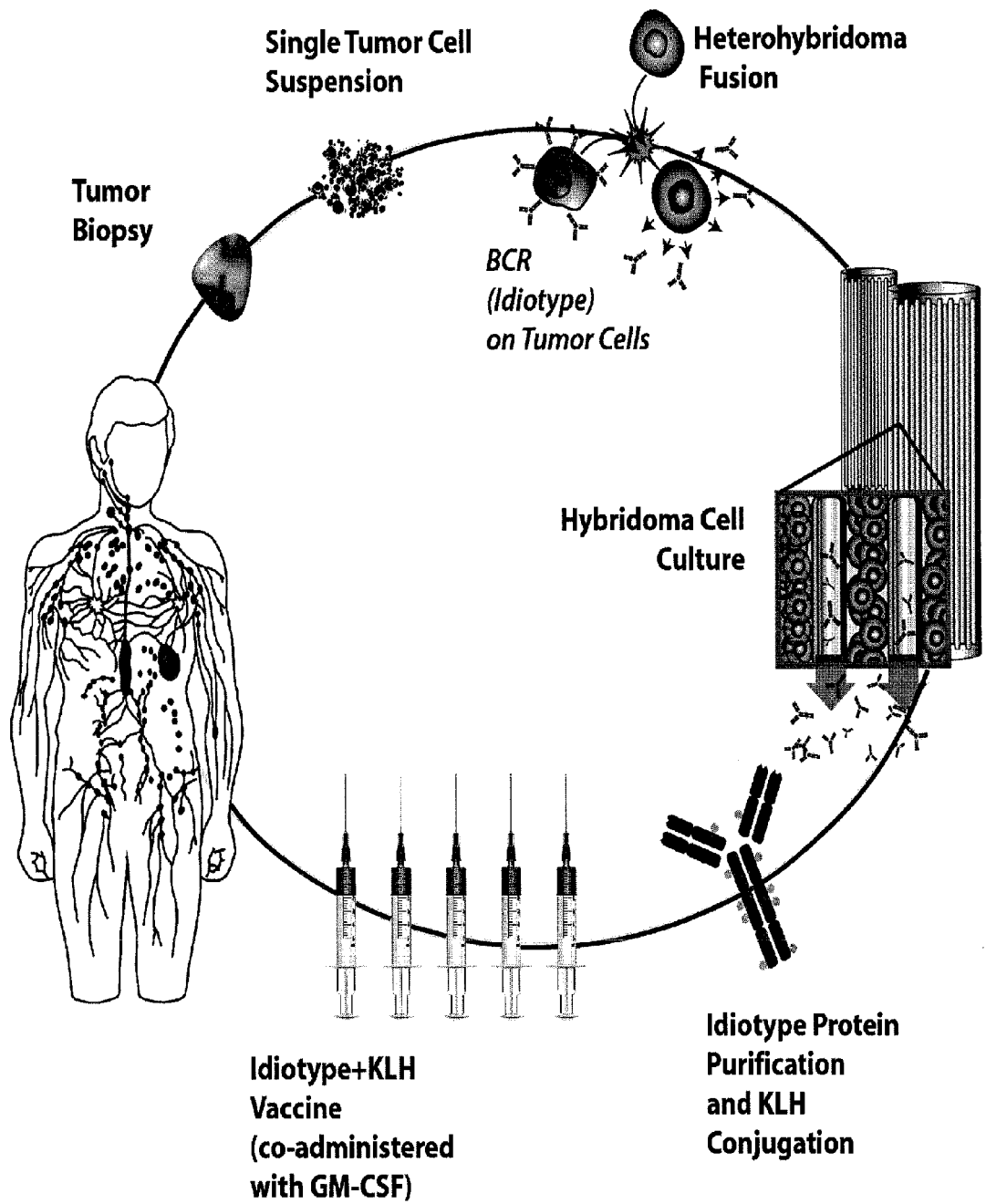
FIG. 2 is a diagram depicting the general methodology of producing a patient-specific idiotype vaccine through the rescue fusion hybridoma method. Referring to the figure (clockwise): beginning with an excisional (>2 cm) lymph node biopsy, tumor cells are fused with a cell line (for example, K6H6 mouse/human heterohybridoma) in order to induce secretion of normally surface-bound tumor immunoglobulin (idiotype or Id). Id-secreting clones are identified by comparing their unique idiotype sequence to the tumor's after which they are cultured (expanded) in a hollow fiber bioreactor system. During culture, supernatant (containing idiotype) is collected until sufficient amounts have been produced to yield adequate dosage of vaccine. This supernatant is purified by affinity chromatography and conjugated (bonded) to a carrier molecule (for example, KLH carrier protein), resulting in a finished vaccine that can be administered to patients.

The potential idiotype-secreting clones of (e) may be produced by various methods, such as hybridoma rescue fusion hybridization (see, for example, FIG. 2), recombinant production (i.e., by introducing a genetic construct into a host cell), or other methods. In some embodiments, hybridoma rescue fusion hybridization is utilized and the hybridoma is produced by fusion of a malignant B-cell obtained from the subject and a murine/human heterohybridoma myeloma cell. In some embodiments, the murine/human heterohybridoma myeloma cell is the K6H6/B5 cell line.

An alternative to hybridoma rescue fusion hybridization for idiotype vaccine production is recombinant production, which typically involves amplification and cloning of the genes endogen the tumor-specific immunoglobulin variable regions, followed by their ligation into plasmid or viral vectors (resulting in a genetic construct) for protein expression in mammalian (e.g., murine lymphoma), insect (e.g., sf9), bacterial (e.g., *Escherichia coli*), or plant (e.g., tobacco) cells (Park H J, Neelapu Br J Haematol. 2008; 142:179-191). When hybridoma methodology is employed, the whole immunoglobuline obtained is virtually identical, at least in amino acid sequence, to that presented by the original tumor, while when recombinant technology is utilized, this can said only for the idiotype itself, as the heavy chains differ significantly.

In some embodiments, the amplification step of (g) is performed in a multiplex manner by polymerase chain reaction (PCR) using barcoded primers, in which each unique barcode corresponds to one amplicon from one potential idiotype-secreting clone.

In some embodiments, the sequencing step of (h) is carried out in a multiplexed manner, in which all the amplicons of the potential idiotype secreting clone amplicon pool are sequenced simultaneously, and in which each barcode identifies the amplicon corresponding to each potential idiotype secreting clone.

The potential idiotype secreting clone amplicon pool may consist of one or more potential idiotype-secreting clones from one (a single) subject, or from a plurality of (multiple) subjects.

In some embodiments, the sequencing step of (h) comprises high-throughput sequencing (HTS), such as pyrosequencing, semiconductor sequencing, or sequencing by synthesis (SBS). In some embodiments, the HTS generates a target of at least 15,000 reads per sample.

In some embodiments, the tumor identifying region of step (b) comprises a rearranged VDJ region of the immunoglobulin heavy chain (IgH) gene, and the potential idiotype secreting clone reads are a quantity of sequences representative of the nucleic acid sequences of the VDJ region present in the tumor cell sample.

Optionally, the method further comprises performing a quality control step on the potential idiotype secreting clone reads of (h). In some embodiments, the quality control step comprises: eliminating any potential idiotype secreting clone reads of (h) that are the result of sequence artifact; and/or assigning a quality score to each potential idiotype secreting clone read of (h), comparing each assigned quality score to a reference threshold quality score, and replacing or annotating any nucleotides in each potential idiotype secreting clone amplicon designated not to have achieved the threshold quality score.

In some embodiments, the selecting step of (l) comprises selecting at least one potential idiotype secreting clone having a tumor identifying region with the identical or substantially similar sequence (e.g., greater than about 80% sequence identity; however, other thresholds may be used) as the most abundant sequence present in the tumor cell sample read.

In some embodiments, the selecting step of (l) comprises selecting at least as many potential idiotype secreting clones having a tumor identifying region with the identical or substantially similar sequence (e.g., greater than about 80% sequence identity; however other thresholds may be used) to as many tumor cell sample read sequences that are required to cover e.g., greater than about 10% of the tumor cell read sequences based on sequence similarity clustering. In some embodiments, the tumor cell sample read sequences that are required to cover greater than about 50% of the tumor cell sample read sequences comprise the most abundant tumor cell sample read sequences.

Optionally, before and/or after administration of the idiotype vaccine to the subject, the method further comprises monitoring the clonality of the B-cell derived malignancy in the subject by:
  (n) obtaining isolated nucleic acid from another cell sample of one or more cells of the B-cell derived malignancy in the subject taken from the subject at a time subsequent to that of the tumor cell sample of (a);
  (o) repeating steps (b)-(l) of the method on the isolated nucleic acid of (n), i.e., from the subsequently taken tumor cell sample;
  (p) determining the abundance of the tumor identifying region sequences in amplicons in the sample of (n) that are similar or substantially similar to (e.g., greater than about 80% sequence identity; however, other thresholds may be used) the tumor identifying region sequence(s) contained in the selected clone(s) used to produce the idiotype vaccine selected in step (l);
  (q) determining the abundance of the tumor identifying region sequences in amplicons in the sample of (n) that were present in the tumor cell sample amplicon but were not contained in the idiotype vaccine prepared in step (m); and
  (r) determining the abundance of the tumor identifying region sequences in amplicons in the sample of (n) that are similar or substantially similar to (e.g., greater than about 80% sequence similarity; however, other thresholds may be used) the tumor identifying region sequence(s) contained in the selected clone(s) of step (l) and used to produce the idiotype vaccine of step (m) but which harbor one or more nucleotide differences in the tumor identifying region ("tumor identifying region mutants").

Optionally, after monitoring the clonality of the B-cell derived malignancy, the method further comprises preparing an updated idiotype vaccine for treatment of the B-cell derived malignancy in the subject, wherein the updated vaccine comprises an idiotype immunoglobulin which is selected to contain one or more of the following:
  (a) the tumor identifying regions sequence(s) contained in the tumor identifying region mutants;
  (b) the tumor identifying region sequence(s) not present in the original tumor cell sample of (a) but present in the subsequent cell sample of (n);
  (c) one or more of the tumor identifying region sequence(s) contained in a prior idiotype vaccine.

In some embodiments, the tumor identifying region comprises a rearranged VDJ region of the immunoglobulin heavy chain (IgH) gene, and the method further comprises monitoring the clonality of the B-cell derived malignancy, wherein the monitoring comprises:
  (n) obtaining isolated nucleic acid from another cell sample of one or more cells of the B-cell derived malignancy in the subject taken from the subject at a time subsequent to that of the cell sample of (a);
  (o) repeating steps (b)-(l) on the isolated nucleic acid of (n);
  (p) determining the abundance of the rearranged VDJ region sequences in amplicons in the sample of (n) that are similar or substantially similar to (e.g., greater than about 80% sequence identity; however, other thresholds may be used) the rearranged VDJ region sequence(s) contained in the selected clone(s) used to produce the idiotype vaccine selected in step (l);
  (q) determining the abundance of the tumor identifying region sequences in amplicons in the sample of (n) that were present in the tumor cell sample amplicon but were not contained in the idiotype vaccine prepared in step (m); and
  (r) determining the abundance of the rearranged VDJ region sequences in amplicons in the sample of (n) that are similar or substantially similar to (e.g., greater than about 80% sequence similarity; however, other thresholds can be used) the rearranged VDJ region sequence(s) contained in the selected clone(s) of step (l) and used to produce the idiotype vaccine of step (m) but which harbor one or more nucleotide differences in the complementary determining region 3 (CDR3) ("CDR3 mutants").

Optionally, the method further comprises preparing an updated idiotype vaccine for treatment of the B-cell derived malignancy in the subject, wherein the updated vaccine comprises an idiotype immunoglobulin which is selected to contain one or more of the following:
  (m) the rearranged VDJ region sequence(s) contained in the CDR3 mutants;
  (n) the rearranged VDJ region sequence(s) not present in the original tumor cell sample but present in the subsequent cell sample of (n);
  (o) one or more of the rearranged VDJ region sequence(s) contained in a prior idiotype vaccine.

As with the earlier version of the vaccine administered to the subject, preparation of the updated vaccine may include conjugating the selected idiotype immunoglobulin with an immunogenic carrier molecule, such as KLH. The method may further comprise administering the updated vaccine to the subject. The updated vaccine may be administered to the subject with or without an adjuvant. In some embodiments, an effective amount of GM-CSF is administered to the subject.

DEFINITIONS

As used herein, an "idiotope" refers to a site on a B-cell receptor that can bind to complementary structures; also on T-cell receptors such sites exist. The collection of idiotopes on one receptor is called "idiotype"; all receptors of a given cell normally have the same specific idiotype. A huge diversity of idiotypes is generated by random somatic rearrangements of genes.

As used herein, a "biomolecule" refers to any molecule that is produced by a biological organism, including large polymeric molecules such as proteins, polysaccharides, lipids, immunoglobulins, and nucleic acids as well as small molecules such as primary metabolites, secondary metabolites, and other natural products.

As used herein, the phrase "next generation sequencing" or NGS refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization. More specifically, the SOLiD Sequencing System of Life Technologies Corp. provides massively parallel sequencing with enhanced accuracy. The SOLiD System and associated workflows, protocols, chemistries, etc. are described in more detail in PCT Publication No. WO 2006/084132, entitled "Reagents, Methods, and Libraries for Bead-Based Sequencing," international filing date Feb. 1, 2006, U.S. patent application Ser. No. 12/873,190, entitled "Low-Volume Sequencing System and Method of Use," filed on Aug. 31, 2010, and U.S. patent application Ser. No. 12/873,132, entitled "Fast-Indexing Filter Wheel and Method of Use," filed on Aug. 31, 2010, the entirety of each of these applications being incorporated herein by reference thereto.

The phrase "sequencing run" refers to any step or portion of a sequencing procedure performed to determine some information relating to at least one biomolecule (e.g., nucleic acid molecule).

It is well known that DNA (deoxyribonucleic acid) is a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. It is also known that certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "nucleic acid sequence," "genomic sequence," "genetic sequence," or "fragment sequence," or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

A "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g., 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

The techniques of "paired-end," "pairwise," "paired tag," or "mate pair" sequencing are generally known in the art of molecular biology (Siegel A. F. et al., *Genomics.* 2000, 68: 237-246; Roach J. C. et al., *Genomics.* 1995, 26: 345-353). These and other sequencing techniques can allow the determination of multiple "reads" of sequence, each from a different place on a single polynucleotide. Typically, the distance (i.e., insert region) between the two reads or other information regarding a relationship between the reads is known. In some situations, these sequencing techniques provide more information than does sequencing two stretches of nucleic acid sequences in a random fashion. With the use of appropriate software tools for the assembly of sequence information (e.g., Mullikin J. C. et al., *Genome Res.* 2003, 13: 81-90; Kent, W. J. et al., *Genome Res.* 2001, 11: 1541-8) it is possible to make use of the knowledge that the "paired-end," "pairwise," "paired tag" or "mate pair" sequences are not completely random, but are known to occur a known distance apart and/or to have some other relationship, and are therefore linked or paired in the genome. This information can aid in the assembly of whole nucleic acid sequences into a consensus sequence.

DNA sequencing can be used to perform the disclosed methods. Comparing the values of the relevant element or elements to a reference set of set involves, but is not limited to, BLAST alignments, megaBLAST alignments, GMAP alignments, BLAT alignments, or a combination thereof. The reference sequence database is, but not limited to, the RefSeq genome database, the transcriptome database, the GENBANK database, or a combination thereof. In an aspect of the present invention, the reference sequence is generated based on identified mutants.

DNA barcodes were first developed as a tool for species-level identifications. Consequently, there is a rapidly growing database of these short sequences from a wide variety of taxa. Correlations have also been drawn between the nucleotide content of the short DNA barcode sequences and the genomes from which they are derived. Consequently, short nucleotide sequences can reliably track information about the composition of the entire genome. Min et al., "DNA barcodes provide a quick preview of mitochondrial genome composition," PLoS One 2(3):e325 (2007).

In the past several years, microarray technologies based on whole genome analysis have been applied to the study of gene expression and/or amplification. Microarrays arose out of the development of large-scale sequencing approaches and generate a far greater volume of data than the data representing the sequences themselves. Ghosh D., "High throughput and global approaches to gene expression," *Comb Chem High Throughput Screen,* 3:411-20 (2000).

The term "parallel sequencing technique" as used herein, refers to any method capable of sequencing multiple templates at one time (i.e., for example, simultaneously). Usually, such techniques are performed by immobilizing either a template or primer on a solid support (i.e., for example, a microarray) configured to support a high throughput process. Pyrosequencing is compatible with most parallel, or massively parallel, sequencing technologies. Fuller C. W., "Rapid parallel nucleic acid analysis" U.S. Pat. No. 7,264,934 (incorporated herein by reference).

As used herein, the term "barcode" refers to a known nucleic acid sequence that allows some feature of a polynucleotide with which the barcode is associated to be identified. In some embodiments, the feature of the polynucleotide to be identified is the sample from which the polynucleotide is derived. In some embodiments, barcodes are at least 3, 4, 5, 6, 7, 8, 9, 10, 11, 12, 13, 14, 15, or more nucleotides in length. In some embodiments, barcodes are shorter than 10, 9, 8, 7, 6, 5, or 4 nucleotides in length. In some embodiments, barcodes associated with some polynucleotides are of different length than barcodes associated with other polynucleotides. In general, barcodes are of sufficient length and comprise sequences that are sufficiently different to allow the identification of samples based on barcodes with which they are associated. In some embodiments, a barcode, and the sample source with which it is associated, can be identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some embodiments, each barcode in a plurality of barcodes differ from every other barcode in the plurality at least three nucleotide positions, such as at least 3, 4, 5, 6, 7, 8, 9, 10, or more positions. In some embodiments, both the first adapter and the second adapter comprise at least one of a plurality of barcode sequences. In some embodiments, barcodes for second adapter oligonucleotides are selected independently from barcodes for first adapter oligonucleotides. In some embodiments, first adapter oligonucleotides and second adapter oligonucleotides having barcodes are paired, such that adapters of the pair comprise the same or different one or more barcodes. In some embodiments, the methods of the invention further comprise identifying the sample from which a target polynucleotide is derived based on a barcode sequence to which the target polynucleotide is joined. In general, a barcode comprises a nucleic acid sequence that when joined to a target polynucleotide serves as an identifier of the sample from which the target polynucleotide was derived.

The term "pyrosequencing" as used herein, refers to any pyrophosphate-based nucleic acid sequencing method. Hyman U.S. Pat. No. 4,971,903 (incorporated herein by reference). This technique is based on the observation that pyrophosphate (PPi) is released upon incorporation of the next correct nucleotide 3' of the primer sequence. For example, when only one of the four nucleotides (i.e., for example, A, T, G, C) is introduced into the reaction at a time, PPi is generated only when the correct nucleotide is introduced. Thus, the production of PPi reveals the identity of the next correct base. Using this process in an iterative fashion results in the identification of the template nucleotide sequence. Pyrosequencing is compatible with most high throughput sequencing techniques, such as using template carrying microbeads deposited in microfabricated picoliter-sized reaction wells. Margulies et al., Nature E-Pub 31 Jul. 2005.

With the advent of high-throughput sequencing, characterization of the nucleic acid world is proceeding at an accelerated pace. Three major high-throughput sequencing platforms are in use today: the Genome Sequencers from Roche/454 Life Sciences [GS-20 or GS-FLX], the 1G Analyzer from Illumina/Solexa and the SOLiD System from Applied Biosystems. Comparison across the three platforms reveals a trade-off between average sequence read length and the number of DNA molecules that are sequenced. At present, the Solexa and SOLiD systems provide many more sequence reads, but render much shorter read lengths than the 454/Roche Genome Sequencers. This makes the 454/Roche platform appealing for use with barcoding technology, as the enhanced read length facilitates the unambiguous identification of both complex barcodes and sequences of interest.

The 454/Roche Genome Sequencers are called pyrosequencers because their sequencing technology is based on the detection of pyrophosphates released during DNA synthesis. A few sequencing runs using 454/Roche's pyrosequencing platform can generate sufficient coverage for assembling entire microbial genomes, for the discovery, identification and quantitation of small RNAs, and for the detection of rare variations in cancers, among many other applications. For analysis of multiple libraries, the currently available 454/Roche pyrosequencers can accommodate up to 16 independent samples, which have to be physically separated using manifolds on the sequencing medium. These separation manifolds occlude wells on the sequencing plate from accommodating bead-bound DNA template molecules, and thus restrict the number of output sequences. To overcome these limitations, a high-information-content barcoding approach can be utilized in which each sample is associated with two uniquely designed barcodes (e.g., 5+-nucleotides in length). The presence of these assigned barcodes allow for independent samples to be pooled together for sequencing, with subsequent bioinformatic segregation of the pyrosequencer output. By not relying on physical separators, this procedure maximizes sequence space and multiplexing capabilities.

The term "simultaneously" as used herein refers to any two or more processes that are occurring more or less at the same time. It is not intended that each process necessarily begin and end precisely together, but only that their respective durations overlap.

The term "pyrosequencing compatible primer" as used herein, refers to any primer, or primer pair, that is capable of supporting nucleic acid amplification using any pyrosequencing technology.

The term "sample assignment" as used herein, refers to any established relationship between the source of a specific nucleotide and an attached barcode. For example, when a unique barcode is cross-referenced with a specific geographic location as to where the nucleotide was obtained, the nucleotide has a sample assignment of that specific geographic location.

The term "amplification products" as used herein, refers to any nucleotide produced by the replication and/or amplification of DNA or RNA. For example, mRNA may be amplified into cDNA by reverse transcriptase. Alternative, a DNA template may undergo amplification of at least one of its strands during a polymerase chain reaction (PCR) thereby producing amplification products the composition of which is dependent upon the primer pair.

The term "sample" as used herein refers to a biological sample that may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis), cDNA (in solution or bound to a solid support) and the like. In some embodiments, the sample is a sample of blood, bone marrow, or lymph node.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

As used herein the term "portion" or "region" when in reference to a protein (as in "a portion or region of a given protein") refers to fragments of that protein. The fragments may range in size from four amino acid residues to the entire amino acid sequence minus one amino acid.

The term "portion" or "region" when used in reference to a nucleotide sequence refers to fragments of that nucleotide sequence. The fragments may range in size from 5 nucleotide residues to the entire nucleotide sequence minus one nucleic acid residue.

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of a target sequence of interest. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "amplification" means the production of additional copies of a nucleic acid sequence and is generally carried out using polymerase chain reaction. Dieffenbach C. W. and G. S. Dveksler (1995) In: PCR Primer, a Laboratory Manual, Cold Spring Harbor Press, Plainview, N.Y.

As used herein, the term "polymerase chain reaction" ("PCR") refers to the method of K. B. Mullis U.S. Pat. Nos. 4,683,195 and 4,683,202, herein incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

PCR assays can used for the identification of clonal B-cell populations. These tests amplify the DNA between primers that target the conserved framework (FR) and joining (J) regions of the immunoglobulin heavy chain (IGH), the variable (V) and joining (J) regions of the immunoglobulin kappa light chain (IGK) and the variable and intragenic regions of the immunoglobulin kappa light chain (IGK). These conserved regions lie on either side of an area within the V-J region where programmed genetic rearrangements occur during maturation of all B and T lymphocytes. The antigen receptor genes that undergo rearrangement are the immunoglobulin heavy chain & light chains genes in B-cells, and the T cell receptor genes in T-cells. Each B- and T-cell has a single productive V-J rearrangement that is unique in both length and sequence. Therefore, when this region is amplified using DNA primers that flank this region, a clonal population of cells yields one or two prominent amplified products (amplicons) within the expected size range. Two products are produced in cases when the initial rearrangement was non-productive and was followed by rearrangement of the other homologous chromosome. In contrast, DNA from a normal or polyclonal (many clones) population produces a bell-shaped curve of amplicon products (Gaussian distribution) that reflect the heterogeneous population of V-J region rearrangements.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxy-ribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers; to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "an oligonucleotide having a nucleotide sequence encoding a gene" means a nucleic acid sequence comprising the coding region of a gene, i.e., the nucleic acid sequence which encodes a gene product. The coding region may be present in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript.

Alternatively, the coding region utilized in the expression vectors of the present invention may contain endogenous enhancers/promoters, splice junctions, intervening sequences, polyadenylation signals, etc. or a combination of both endogenous and exogenous control elements.

The term "transfection" or "transfected" refers to the introduction of foreign DNA into a cell.

As used herein, the terms "nucleic acid molecule encoding", "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products which control the expression of other genes (e.g., transcription factors).

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences. Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

Genes encoding immunoglobulin heavy chain (IGH) molecules are assembled from multiple polymorphic gene segments that undergo rearrangement and selection during B cell development. Rearrangement of these variable (V), diversity (D), and joining (J) genetic segments result in VDJ products of unique length and sequence. Clonal IGH rearrangements can be rapidly identified through analyses of the size distributions of DNA products amplified from conserved sequences that flank this region. For example, DNA isolated from a normal polyclonal population of B cells produces a Gaussian distribution (bell-shaped size curve) of amplified products, whereas DNA amplified from a clonal B cell population generates one or two product(s) of unique size that reflect proliferation of a single rearranged clone. Southern blot analysis requires 1-2 weeks, is significantly less sensitive, and requires approximately one hundred times more DNA than PCR-based tests, which can be completed in 4-5 hours. In addition, tests of samples previously designated Quantity Not Sufficient (QNS), such as formalin-fixed, paraffin-embedded tissue sections, routinely produce a valid result.

Genomic DNA can be amplified using three master mixes that target the three conserved framework regions (FR1, FR2, and FR3) of the IGH gene, and the joining (J) region. These regions flank the unique, hypervariable, antigen-binding, complementarity determining region 3 (CDR3). All positive and negative DNA controls, as well as an internal Amplification Control master mix, are included. The limit of detection of this assay is better than one clonal B cell in a background of a hundred normal cells. Clonality is indicated if one or more of the three framework master mixes generates clonal band(s). PCR products of the FR1, FR2, and FR3 master mixes are differentially labeled with 6FAM, NED, and HEX, respectively, and can be analyzed using any platform that has the ability to detect these fluorochromes such as the Applied Biosystems ABI 310 and ABI 3100.

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabead), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all incorporated by reference herein). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

The terms "eliminating," "substantially reducing," "treating," and "treatment," as used herein, refer to therapeutic or preventative measures described herein. The methods of "eliminating or substantially reducing" employ administration to a subject having a B-cell malignancy. In some embodiments, the term "eliminating" refers to a complete remission of a B-cell malignancy in a subject treated using the methods described herein.

The terms "B lymphocyte" and "B cell," as used interchangeably herein, are intended to refer to any cell within the B cell lineage as early as B cell precursors, such as pre-B cells B220$^+$ cells which have begun to rearrange Ig VH genes and up to mature B cells and even plasma cells such as, for example, plasma cells which are associated with multiple myeloma. The term "B-cell," also includes a B-cell derived cancer stem cell, i.e., a stem cell which is capable of giving rise to non-Hodgkin's lymphoma, Hodgkin's lymphoma, chronic lymphocytic leukemia, mantle cell lymphoma or multiple myeloma. Such cells can be readily identified by one of ordinary skill in the art using standard techniques known in the art and those described herein.

The terms "B-cell malignancy" and "B-cell derived malignancy" refer to a malignancy arising from aberrant replication of B cells. B-cell malignancies include, for example, non-Hodgkin's lymphoma, chronic lymphocytic leukemia (CLL), small lymphocytic lymphoma, multiple myeloma, mantle cell lymphoma, B-cell prolymphocytic leukemia, lymphoplasmocytic lymphoma, splenic marginal zone lymphoma, marginal zone lymphoma (extra-nodal and nodal), follicular lymphoma (grades I, II, III, or IV), diffuse large B-cell lymphoma, mediastinal (thymic) large B-cell lymphoma, intravascular large B-cell lymphoma, primary effusion lymphoma, Burkitt lymphoma/leukemia. The B-cell malignancy may be a mature B-cell lymphoma. Examples of mature B-cell lymphomas include B-cell chronic lymphocytic leukemia/small lymphocytic lymphoma, B-cell prolymphocytic leukemia, lymphoplasmacytic lymphoma, splenic marginal zone B-cell lymphoma (½ villous lymphocytes), hairy cell leukemia, plasma cell myeloma/plasmacytoma, extranodal marginal zone B-cell lymphoma of MALT type, nodal marginal zone B-cell lymphoma (½ monocytoid B cells), follicular lymphoma, mantle-cell lymphoma, diffuse large B-cell lymphoma, mediastinal large B-cell lymphoma, primary effusion lymphoma, Burkitt lymphoma/Burkitt cell leukemia.

The mature B-cell lymphoma may be a variant malignancy, for example, B-cell chronic lymphocytic leukemia/small lymphocytic lymphoma with monoclonal gammopathy/plasmacytoid differentiation, hairy cell leukemia variant, cutaneous follicle center lymphoma, diffuse follicle center lymphoma, blastoid mantle-cell lymphoma, morphologic variant of diffuse large B-cell lymphoma (for example, centroblastic, immunoblastic, T-cell/histiocyte-rich, lymphomatoid granulomatosis type, anaplastic large B-cell, plasmablastic) or subtype of diffuse large B-cell lymphoma (for example, mediastinal (thymic) large B-cell lymphoma, primary effusion lymphoma, intravascular large B-cell lymphoma), morphologic variant of Burkitt lymphoma or Burkitt cell leukemia (for example, Burkitt-like lymphoma/leukemia, Burkitt lymphoma/Burkitt cell leukemia with plasmacytoid differentiation (AIDS-associated), or clinical or genetic subtype of Burkitt lymphoma/Burkitt cell leukemia (for example, endemic, sporadic, immunodeficiency-associated).

The terms "immunoglobulin" and "antibody" (used interchangeably herein) include a protein having a basic four-polypeptide chain structure consisting of two heavy and two light chains, said chains being stabilized, for example, by interchain disulfide bonds, which has the ability to specifically bind an antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind an antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable," based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions." The "constant" domains of an antibody light chain are referred to interchangeably as "light chain constant regions," "light chain constant domains," "CL" regions or "CL" domains. The "constant" domains of an antibody heavy chain are referred to interchangeably as "heavy chain constant regions," "heavy chain constant domains," "CH" regions or "CH" domains). The "variable" domains of an antibody light chain are referred to interchangeably as "light chain variable regions," "light chain variable domains," "VL" regions or "VL" domains). The "variable" domains of an antibody heavy chain are referred to interchangeably as "heavy chain constant regions," "heavy chain constant domains," "VH" regions or "VH" domains).

Immunoglobulins or antibodies can exist in monomeric or polymeric form, for example, IgM antibodies which exist in pentameric form and/or IgA antibodies which exist in monomeric, dimeric or multimeric form. Other than "bispecific" or "bifunctional" immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, (1990) *Clin. Exp. Immunol.* 79:315-321; Kostelny et al., (1992) *J. Immunol.* 148:1547-1553.

The term "antigen-binding portion" of an antibody (or "antibody portion") includes fragments of an antibody that retain the ability to specifically bind to an antigen (e.g., a B-cell specific antigen). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P. et al., (1993) *Proc. Natl. Acad. Sci. USA*

90:6444-6448; Poljak, R. J. et al., (1994) *Structure* 2:1121-1123). Still further, an antibody or antigen-binding portion thereof may be part of a larger immunoadhesion molecule, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M. et al., (1995) *Human Antibodies and Hybridomas* 6:93-101) and use of a cysteine residue, a marker peptide and a C-terminal polyhistidine tag to make bivalent and biotinylated scFv molecules (Kipriyanov, S. M. et al., (1994) *Mol. Immunol.,* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. Preferred antigen binding portions are complete domains or pairs of complete domains.

"Specific binding," "specifically binds," "specific for", "selective binding," and "selectively binds," as used herein, mean that the compound, e.g., antibody or antigen-binding portion thereof, exhibits appreciable affinity for a particular antigen or epitope and, generally, does not exhibit significant cross-reactivity with other antigens and epitopes. "Appreciable" or preferred binding includes binding with an affinity of at least $10^6$, $10^7$, $10^8$, $10^9$ $M^{-1}$, or $10^{10}$ $M^{-1}$. Affinities greater than $10^7 M^{-1}$, preferably greater than $10^8$ $M^{-1}$ are more preferred. Values intermediate of those set forth herein are also intended to be within the scope of the present invention and a preferred binding affinity can be indicated as a range of affinities, for example, $10^6$ to $10^{10}$ $M^{-1}$, preferably $10^7$ to $10^{10}$ $M^{-1}$, more preferably $10^8$ to $10^{10}$ $M^{-1}$. An antibody that "does not exhibit significant cross-reactivity" is one that will not appreciably bind to an undesirable entity (e.g., an undesirable proteinaceous entity). For example, in one embodiment, an antibody or antigen-binding portion thereof, that specifically binds to a B-cell specific antigen, such as, for example, CD-20 or CD-22, will appreciably bind CD-20 or CD-22, but will not significantly react with other non-CD-20 or non-CD-22 proteins or peptides. Specific or selective binding can be determined according to any art-recognized means for determining such binding, including, for example, according to Scatchard analysis and/or competitive binding assays.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The term "human antibody" includes antibodies having variable and constant regions corresponding to human germline immunoglobulin sequences as described by Kabat et al. (See Kabat, et al., (1991) *Sequences of proteins of Immunological Interest, Fifth Edition,* U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In a preferred embodiment, these replacements are within the CDR regions as described in detail below.

The term "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor, L. D. et al., (1992) *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences (See Kabat E. A., et al., (1991) *Sequences of Proteins of Immunological Interest, Fifth Edition,* U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of the selective mutagenesis approach or backmutation or both.

An "isolated antibody" includes an antibody that is substantially free of other antibodies having different antigenic specificities (e.g., an isolated antibody that specifically binds a B-cell specific antigen and is substantially free of antibodies or antigen-binding portions thereof that specifically bind other antigens, including other B-cell antigens). An isolated antibody that specifically binds a B-cell specific antigen may bind the same antigen and/or antigen-like molecules from other species. Moreover, an isolated antibody may be substantially free of other cellular material and/or chemicals.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

The terms "idiotype," "Id," and "idiotypic determinant," as used herein, refer to an epitope in the hypervariable region of an immunoglobulin. Typically, an idiotype or an epitope thereof is formed by the association of the hypervariable or complementarity determining regions (CDRs) of VH and VL domains.

The terms "anti-idiotype" and "anti-Id," refer to an antibody, or antigen-binding portion thereof, that binds one or more idiotypes present on an antibody.

The term "autologous idiotype vaccine" refers to a composition, the active ingredient of which is an immunogenic molecule that is preferably capable of inducing an immune response against a B-cell idiotype derived from the same subject to which it is administered. In some embodiments, the immunogenic molecule in a vaccine used in the methods of the present invention is a normal product of a subject's B cells that happens to be expressed clonally on the cancer cells (e.g., cells derived from a Hodgkin's lymphoma or non-Hodgkin's lymphoma or chronic lymphocytic leukemia, mantle cell lymphoma or multiple myeloma) and serves as a unique a target for immune attack. In some embodiments, the vaccine comprises an IgM anti-Id immunoglobulin. In some embodiments, an "autologous idiotype vaccine," is capable of eliciting an immune response against a B-cell idiotype derived from a subject having non-Hodgkin's lymphoma. In another embodiment, an "autologous idiotype vaccine," is capable of eliciting an immune response against a B-cell idiotype derived from a subject having Hodgkin's lymphoma. In yet another embodiment, an "autologous idiotype vaccine," is capable of eliciting an immune response against a B-cell idiotype derived from a subject having chronic lymphocytic leukemia. In a further embodiment, an "autologous idiotype vaccine," is capable of eliciting an immune response against a B-cell idiotype derived from a subject having multiple myeloma. In a yet further embodiment, an "autologous idiotype vaccine," is capable of eliciting an immune response against a B-cell idiotype derived from a subject having mantle cell lymphoma. In some embodiments of the present invention, an "autologous idiotype vaccine," is used for the treatment of a B-cell derived cancer in combination with other immune therapeutics such as, for example, monoclonal antibodies that selectively bind B-cell specific antigens. In some embodiments, an "autologous idiotype vaccine" includes an antigen associated with a B-cell derived cancer in a subject (e.g., non-Hodgkin's lymphoma, Hodgkin's lymphoma, chronic lymphocytic leukemia, mantle cell lymphoma or multiple myeloma) linked to KLH (keyhole limpet hemocyanin, a carrier protein). In some embodiments of the present invention, an autologous idiotype vaccine is administered in conjunction with GM-CSF, or another a different adjuvant, and optionally subsequently re-administered, as a booster, one or times with or without the adjuvant.

The term "granulocyte monocyte colony stimulating factor" or "GM-CSF" refers to a hematopoeitic growth factor that stimulates the development of committed progenitor cells to neutrophils and enhances the functional activities of neutrophils. It is produced in response to specific stimulation by a variety of cells including macrophages, fibroblasts, endothelial cells and bone marrow stroma. Either purified GM-CSF or recombinant GM-CSF, for example, recombinant human GM-CSF (R & D SYSTEMS, INC, Minneapolis, Minn.) or sargramostim (LEUKINE, BAYER HEALTHCARE Pharmaceuticals, Wayne, N.J.) can be used in the methods described herein.

The phrase "an effective amount of granulocyte monocyte colony stimulating factor" refers to an amount of granulocyte monocyte colony stimulating factor, which upon a single or multiple dose administration to a subject, induces or enhances an immune response in the subject (e.g., as an adjuvant). In some embodiments, 50 µg/m$^2$/day to about 200 µg/m$^2$/day (e.g., 100 µg/m$^2$/day) granulocyte monocyte colony stimulating factor is administered to the subject. In some embodiments, "an effective amount of granulocyte monocyte colony stimulating factor" refers to a daily administration of 5 µg/kg of the granulocyte colony stimulating factor.

As used herein, the term "epitope" or "antigenic determinant" or "idiotypic determinant" refers to a site on an antigen to which an immunoglobulin (or antigen binding fragment thereof) can specifically bind. Epitopes can be formed both from contiguous amino acids or noncontiguous amino acids juxtaposed by tertiary folding of a protein. Epitopes found on the Fab (variable) region of immunoglobulins are referred to as "idiotypic determinants" and comprise the immunoglobulin's "idiotype". Epitopes formed from contiguous amino acids are typically retained on exposure to denaturing solvents, whereas epitopes formed by tertiary folding are typically lost on treatment with denaturing solvents. In the case of proteinaceous antigens, an epitope typically includes at least 3, 4, 5, 6, 7, 8, 9, 10, 11, 12, 13, 14 or 15 amino acids in a unique spatial conformation. Methods of determining spatial conformation of epitopes include, for example, x-ray crystallography and 2-dimensional nuclear magnetic resonance. See, for example, Epitope Mapping Protocols in Methods in Molecular Biology, Vol. 66, G. E. Morris, Ed. (1996).

The term "domain" refers to a globular region of a heavy or light chain polypeptide comprising peptide loops (e.g., comprising 3 to 4 peptide loops) stabilized, for example, by beta-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. "Constant" domains on the light chain are referred to interchangeably as "light chain constant regions", "light chain constant domains", "CL" regions or "CL" domains). "Constant" domains on the heavy chain are referred to interchangeably as "heavy chain constant regions", "heavy chain constant domains", "CH" regions or "CH" domains). "Variable" domains on the light chain are referred to interchangeably as "light chain variable regions", "light chain variable domains", "VL" regions or "VL" domains). "Variable" domains on the heavy chain are referred to interchangeably as "heavy chain variable regions", "heavy chain variable domains", "VH" regions or "VH" domains).

The term "region" refers to a part or portion of an antibody chain or antibody chain domain (for example, a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein. As used herein, a "region" of an antibody is inclusive of regions existing in isolation (as antibody fragments) and as part of whole (intact) or complete antibodies. Thus, for example, an idiotype immunoglobulin comprising "at least an IgM constant region" encompasses embodiments in which the idiotype immunoglobulin is composed of only the constant region of the IgM (and, optionally, other non-IgM components), as well as embodiments in which the idiotype immunoglobulin is composed of more of the IgM than just the constant region (and, optionally, other non-IgM components).

As used herein, the terms "constant region" or "fragment crystallizable region" (Fc region) refers to that portion of the antibody (the tail region) that interacts with cell surface receptors called Fc receptors and some proteins of the complement system, and is composed of two heavy chains that contribute two or three constant domains depending on the class of the antibody (Janeway C A, Jr et al. (2001). *Immunobiology*. (5th ed.). Garland Publishing). In IgG, IgA and IgD antibody isotypes, the Fc region is composed of two identical protein fragments, derived from the second and third constant domains of the antibody's two heavy chains; IgM and IgE Fc regions contain three heavy chain constant domains ($C_H$ domains 2-4) in each polypeptide chain. The Fc regions of IgGs bear a highly conserved N-glycosylation site (Janeway C A, Jr et al. (2001). *Immunobiology*. (5th ed.); Garland Publishing Rhoades R A, Pflanzer R G (2002). *Human Physiology* (4th ed.). Thomson Learning). The other part of an antibody, called the Fab region, contains variable sections that define the specific target that the antibody can bind. By contrast, the Fc region of all antibodies in a class are the same for each species; they are constant rather than variable. The terms "Fc region" and "Fab region" encompass these regions existing in isolation (as antibody fragments) and as part of a whole (intact) or complete, full-length antibody.

The terms "polynucleotide" and "nucleic acid molecule" are used interchangeably herein to refer to a polymeric form of nucleotides of any length, which contain deoxyribonucleotides, ribonucleotides, and analogs in any combination analogs. Polynucleotides may have any three-dimensional structure, and may perform any function, known or unknown. The term "nucleic acid molecule" includes double-, single-stranded, and triple-helical molecules. Unless otherwise specified or required, any embodiment of the invention described herein that is a nucleic acid molecule encompasses both the double-stranded form and each of two complementary single-stranded forms known or predicted to make up the double stranded form. In some embodiments, the nucleic acid molecule encodes an epitope or an antigen.

The following are non-limiting examples of nucleic acid molecules: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A nucleic acid molecule may be further modified after polymerization, such as by conjugation with a labeling component. Other types of modifications included in this definition are caps, substitution of one or more of the naturally occurring nucleotides with an analog, and introduction of means for attaching to proteins, metal ions, labeling components, other nucleic acid molecules, or a solid support.

The terms "polypeptide", "peptide" and "protein" are used interchangeably herein to refer to polymers of amino acids of any length. The polymer may be linear or branched, it may comprise modified amino acids or amino acid analogs, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component.

The term "fusion polypeptide" refers to a polypeptide comprising regions in a different position in the sequence than occurs in nature. The regions may normally exist in separate proteins and are brought together in the fusion polypeptide; or they may normally exist in the same protein but are pieced in a new arrangement in the fusion polypeptide. Fusion polypeptides can be produced by linking two or more polypeptides together (for example, covalently), or by expressing nucleic acids encoding each fusion partner within a host cell, for example.

The term "adjuvant" refers to a substance incorporated into or administered simultaneously with an antigen which potentiates the immune response in response to that antigen but does not in itself confer immunity. A tetanus, diphtheria, and pertussis vaccine, for example, contains minute quantities of toxins produced by each of the target bacteria, but also contains some aluminum hydroxide. Aluminum salts are common adjuvants in vaccines sold in the United States and have been used in vaccines for over 70 years. The body's immune system develops an antitoxin to the bacteria's toxins, not to the aluminum, but would not respond enough without the help of the aluminum adjuvant. An adjuvant can also include cytokines such as granulocyte-monocyte colony stimulating factor (GM-CSF). In some cases, e.g., immunization of a subject against normally non-immunogenic tumor-derived idiotypes, foreign (non-self) carrier protein immunogens such as keyhole limpet hemocyanin (KLH), can also potentiate the immune response and serve as adjuvants.

B-Cell Malignancy Sampling and Isotyping

Samples of malignant cells (e.g., tumor cells) can be obtained from a subject by biopsy, fine-needle aspiration, or apheresis, for example. The immunoglobulin may be present on the malignant cell surface, within the malignant cell cytoplasm, or in the subject's blood. The method of collection will depend upon where the immunoglobulin-bearing cells or secreted immunoglobulin molecules are found. For example, depending upon the malignancy, samples can be obtained from lymph nodes, extra-nodal tissue, spleen, bone marrow, or blood (Alvarez-Vallina L. et al., *Journal of Immunotherapy*, 1995, 17:194-198).

Malignant cells can be isotyped by flow cytometry (Zabelegui N. et al., *haeamatologica*, 2004, 89(5):541-546). Antibodies specific for various isotypes are commercially available. For example, human anti-IgM antibodies are available from Miltenyi Biotec (Auburn Calif.). Other methods such as immunofluorescence, immunohistochemistry of sections (e.g., from a biopsy), sequencing of the constant region on the heavy chain, immunoblot, etc. (Fakhrjou A. et al., *Pakistan Journal of Biological Sciences*, 2010, 13(4): 194-197).

In some embodiments, the B-cell malignancy exhibits a predetermined immunoglobulin isotype or isotypes that is not an IgM isotype (a non-IgM immunoglobulin). In some embodiments, the B-cell the malignancy exhibits a predetermined immunoglobulin isotype or isotypes that is an IgM isotype (an IgM immunoglobulin). In some embodiments, the non-IgM immunoglobulin is IgG, IgA, IgD, IgE, or any combination of two or more of the foregoing (for example, IgM/IgA or IgM/IgG). In some embodiments, the non-IgM immunoglobulin is IgG1, IgG2, IgG3, IgG4, IgA1, IgA2, IgE, IgD, or any combination of the foregoing.

Exemplary Disorders

Exemplary disorders which may be treated using the methods of the invention include B-cell malignancies and in particular, B-cell derived cancers or neoplasms such as, for example, non-Hodgkin's lymphoma, Hodgkin's lymphoma, chronic lymphocytic leukemia, mantle cell lymphoma and multiple myeloma. Additional B-cell derived cancers include, for example, B-cell prolymphocytic leukemia, lymphoplasmocytic leukemia, splenic marginal zone lymphoma, marginal zone lymphoma (extra-nodal and nodal), plasma cell neoplasms (e.g., plasma cell myeloma, plasmacytoma, monoclonal immunoglobulin deposition diseases, heavy chain diseases), and follicular lymphoma (e.g., Grades I, II, III, or IV).

In some embodiments, a malignancy treated using the methods of the present invention is a B-cell derived malignancy associated with the expression of one or more B-cell specific antigens such as, for example, CD3d, CD5, CD6, CD9, CD19, CD20, CD21, CD22, CD23, CD24, CD27, CD28, CD37, CD38, CD40, CD45, CD46, CD48, CD53, CD69, CD70, CD72, CD73, CD79a, CD79b, CD80, CD81, CD83, CD85a, CD85d, CD85e, CD85h, CD85i, CD85j, CD85k, CD86, CD96, CD98, CD100, CD121b, CD124, CD127, CD132, CD150, CD152, CD154, CD157, CD166, CD169, CD179a, CD179b, CD180, CD185, CD196, CD197, CD205, CDw210a, CD213a1, CD257, CD267, CD268, CD269, CD274, CD275, CD276, CD278, CD279, CD300a, CD300c, CD307, CD314, CD316, CD317, CD319, CD320, CDw327, and CD331. In a particular embodiment, a cancer treated using the methods of the invention is associated with the expression of CD-20. In another embodiment, a cancer treated using the methods of the invention is associated with the expression of CD-22. In yet another embodiment, a cancer treated using the methods of the invention is associated with the expression of both CD-20 and CD-22.

In some embodiments, a cancer treated using the methods of the invention is non-Hodgkin's lymphoma or NHL. Non-Hodgkin's lymphoma or NHL, is a cancer of the lymphoid tissue which is formed by several types of immune cells including B-cells and T-cells. About 85% of the non-Hodgkin's lymphomas are derived from B-cells. NHL is thought to occur when B-cells, which produce antibodies, begin to grow abnormally. In some embodiments, non-Hodgkin's lymphoma treated using the methods of the invention is associated with the expression of CD-20 on B-cells. In other embodiments, non-Hodgkin's lymphoma is associated with the expression of CD-22. In yet other embodiments, non-Hodgkin's lymphoma is associated with the expression of both CD-20 and CD-22.

In some embodiments, a cancer treated using the methods of the invention is Hodgkin's lymphoma, also referred to as Hodgkin's disease. The cancer cells in Hodgkin's disease are called Reed-Sternberg cells, after the two doctors who first described them in detail. Under a microscope they look different from cells of non-Hodgkin's lymphomas and other cancers, and are believed to be a type of malignant B lymphocyte.

In some embodiments, a cancer treated using the methods of the invention is chronic lymphocytic leukemia (CLL) which is derived from a small B lymphocyte. CLL is mostly found in the blood and in the bone marrow.

In further embodiments, a cancer treated using the methods of the invention is mantle cell lymphoma.

In some embodiments, the B-cell malignancy is multiple myeloma, associated with uncontrolled proliferation of antibody producing cells in the plasma, which develop from B-cells.

In some embodiments, the B-cell malignancy is non-Hodgkin's lymphoma, chronic lymphocytic leukemia (CLL), small lymphocytic lymphoma, multiple myeloma, mantle cell lymphoma, B-cell prolymphocytic leukemia, lymphoplasmocytic lymphoma, splenic marginal zone lymphoma, marginal zone lymphoma (extra-nodal and nodal), follicular lymphoma (grades I, II, III, or IV), diffuse large B-cell lymphoma, mediastinal (thymic) large B-cell lymphoma, intravascular large B-cell lymphoma, primary effusion lymphoma, or Burkitt lymphoma/leukemia. In some embodiments, the B-cell malignancy is a mature B-cell lymphoma. In some embodiments, the mature B-cell lymphoma is B-cell chronic lymphocytic leukemia/small lymphocytic lymphoma, B-cell prolymphocytic leukemia, lymphoplasmacytic lymphoma, splenic marginal zone B-cell lymphoma (½ villous lymphocytes), hairy cell leukemia, plasma cell myeloma/plasmacytoma, extranodal marginal zone B-cell lymphoma of MALT type, nodal marginal zone B-cell lymphoma (½ monocytoid B cells), follicular lymphoma, mantle-cell lymphoma, diffuse large B-cell lymphoma, mediastinal large B-cell lymphoma, primary effusion lymphoma, or Burkitt lymphoma/Burkitt cell leukemia.

In some embodiments, the mature B-cell lymphoma is a variant malignancy, for example, B-cell chronic lymphocytic leukemia/small lymphocytic lymphoma with monoclonal gammopathy/plasmacytoid differentiation, hairy cell leukemia variant, cutaneous follicle center lymphoma, diffuse follicle center lymphoma, blastoid mantle-cell lymphoma, morphologic variant of diffuse large B-cell lymphoma (for example, centroblastic, immunoblastic, T-cell/histiocyte-rich, lymphomatoid granulomatosis type, anaplastic large B-cell, plasmablastic) or subtype of diffuse large B-cell lymphoma (for example, mediastinal (thymic) large B-cell lymphoma, primary effusion lymphoma, intravascular large B-cell lymphoma), morphologic variant of Burkitt lymphoma or Burkitt cell leukemia (for example, Burkitt-like lymphoma/leukemia, Burkitt lymphoma/Burkitt cell leukemia with plasmacytoid differentiation (AIDS-associated), or clinical or genetic subtype of Burkitt lymphoma/Burkitt cell leukemia (for example, endemic, sporadic, immunodeficiency-associated).

Exemplary Autologous Idiotype Vaccines

In various embodiments of the methods of the present invention, an autologous idiotype vaccine is produced using a hybridoma technology. For example, a hybridoma cell-line may be developed which contains a tumor-specific antigen derived from a patient, which is unique to that patient and found exclusively on the surface of a B-lymphocyte associated with a B-cell derived cancer such as, for example, non-Hodgkin's lymphoma, Hodgkin's lymphoma, chronic lymphocytic leukemia, mantle cell lymphoma or multiple myeloma, and which is absent or expressed in decreased amounts in normal B-lymphocytes and other cells.

In some embodiments, an "autologous idiotype vaccine" includes an antigen associated with a B-cell derived cancer in a subject (for example, non-Hodgkin's lymphoma, Hodgkin's lymphoma, chronic lymphocytic leukemia, mantle cell lymphoma or multiple myeloma) linked to a carrier molecule, such as a carrier protein. Preferably, the carrier molecule is immunogenic, such as the immunogenic carrier protein KLH ((keyhole limpet hemocyanin) Kwak L W et al., *N Engl. J. Med.*, 327:1209-1215 (1992); Hsu F J et al.,

*Blood*, 89:3129-3135 (1997); Schumacher K, J. *Cancer Res. Clin. Oncol.*, 127(Suppl 2):R1-R2 (2001)).

In some embodiments, the autologous idiotype vaccine comprises an antigen associated with a B-cell derived malignancy in the subject, and wherein the antigen is produced by a hybridoma (see, for example, Lee S T et al., *Expert Opin Biol Ther*, 7(1):113-122 (2007); Flowers C R, *Expert Rev Vaccines*, 6(3):307-317 (2007); Neelapu S S and L W Kwak, *Hematology*, 243-249, (2007); Lee S-T. et al., *Yonsei Medical Journal*, 48(1):1-10 (2007); Ruffini P A et al., *Haematologica*, 87:989-1001 (2002), which are each incorporated herein by reference in their entirety). In some embodiments, the hybridoma is produced by fusion of a cancerous B-cell obtained from the subject and a murine/human heterohybridoma myeloma cell, such as the K6H6/B5 cell line. In some embodiments, the antigen-producing hybridoma is grown in a hollow-fiber bioreactor, such as those described in one or more of International Patent Publications WO 2007/139748 (Biovest International, Inc., filed May 21, 2007); WO 2007/139742 (Biovest International, Inc., filed May 21, 2007); WO 2007/139746 (Biovest International, Inc., filed May 21, 2007); WO 2007/136821 (Biovest International, Inc., filed May 21, 2007); and WO 2007/139747 (Biovest International, Inc., filed May 21, 2007), each of which are incorporated herein by reference in their entirety). The antigen can then be collected from the hollow-fiber bioreactor and purified (e.g., by affinity chromatography) prior to administration to the subject.

Preferably, in both the initial treatment with the autologous idiotype vaccine and in any (optional) booster doses of the autologous idiotype vaccine, the purified antigen is conjugated to a carrier molecule, such as an immunogenic carrier protein (e.g., KLH), prior to administration to the subject.

In some embodiments, the autologous idiotype vaccine comprises a chimeric idiotype immunoglobulin comprising at least an IgM constant region, and a variable region derived from a non-IgM immunoglobulin expressed by the malignancy. In some embodiments, the autologous idiotype vaccine comprises a chimeric idiotype immunoglobulin comprising at least an IgM constant region, and a variable region derived from an IgM immunoglobulin expressed by the malignancy. The chimeric idiotype immunoglobulin can be produced recombinantly by introducing a genetic construct into a host cell, wherein the genetic construct comprises a nucleic acid sequence encoding the IgM constant region and a nucleic acid sequence encoding the variable region of the immunoglobulin expressed by the malignant cell, wherein the isotype of the immunoglobulin is not IgM (the non-IgM variable region), and wherein the nucleic sequences are expressed by the host cell.

The type of host cell used to produce the chimeric idiotype immunoglobulin may be any capable of expressing the nucleic acids encoding the IgM constant region and/or variable region of the immunoglobulin expressed by the malignant cell. For example, the host cell may be a mammalian cell, insect cell, bacterial cell, plant cell, viral cell, or fungal cell (see, for example, Bendandi, M. et al., "Rapid, high-yield production in plants of individualized idiotype vaccines for non-Hodgkin's lymphoma," *Ann Oncol.*, 21(12):2420-2427 (2010); Bertinetti, C. et al., "Cloning of idiotype immunoglobulin genes in B cell lymphomas by anchored PCR and production of individual recombinant idiotype vaccines in *Escherichia coli*," *Eur J Haematol*, 77(5):395-402 (2006); Tchoudakova, A. et al., "High level expression of functional human IgMs in human PER.C6 cells," *MAbs*, (2):163-71 (2009); Wood, C. R. et al., "High level synthesis of immunoglobulins in Chinese hamster ovary cells," *J Immunol*, 145(9): p. 3011-6 (1990)). Host cells useful for expression of polynucleotides encoding the immunoglobulin domains may be primary cells or cells of cell lines. The host cells may be tumor cells (transformed cells) or non-tumor cells. Mammalian cell lines available as hosts for expression are known in the art and are available from depositories such as the American Type Culture Collection. These include but are not limited to HeLa cells, human embryonic kidney (HEK) cells, Chinese hamster ovary (CHO) cells, baby hamster kidney (BHK) cells, and others.

Both prokaryotic and eukaryotic host cells may be used for expression of desired coding sequences when appropriate control sequences (e.g., promoter sequences) that are compatible with the designated host are used. For example, among prokaryotic hosts, *Escherichia coli* may be used. Also, for example, expression control sequences for prokaryotes include but are not limited to promoters, optionally containing operator portions, and ribosome binding sites. Eukaryotic hosts include yeast, insect, and mammalian cells in culture systems. *Pichia pastoris, Saccharomyces cerevisiae* and *S. carlsbergensis* are commonly used yeast hosts.

As indicated above, the type of host cell used may be, for example, a mammalian cell, insect cell, bacterial cell, plant cell, viral cell, or fungal cell. *Trichoplusia ni* and *Spodoptera frugiperda* (Sf9) are examples of insect cells that may be used. The baculovirus expression system is an attractive alternative to antibody production in *E. coli* and mammalian cells, for example. The baculovirus/insect cell system also circumvents solubility problems that may be encountered when recombinant proteins are overexpressed in prokaryotes. In addition, insect cells contain the eukaryotic post-translational modification machinery responsible for correct folding, disulfide formation, glycosylation, P-hydroxylation, fatty acid acylation, prenylation, phosphorylation and amidation not present in prokaryotes.

Exemplary Antibodies for Combination or Adjunctive Treatment

In various methods of the present invention, malignancies derived from B-cells can be treated using a combination of an autologous idiotype vaccine with one or more other therapies, such as a monoclonal antibody. The combination therapy may be consecutive (e.g., antibody therapy followed by autologous idiotype vaccine therapy) or contemporaneous. In some embodiments, malignancies derived from B-cells can be treated using a combination of an autologous idiotype vaccine with a monoclonal antibody which selectively binds a B-cell specific antigen. Examples of monoclonal antibody therapies include rituximab, tositumomab, ibritumomab tiuxetan, epratuzumab alemtuzumab, (see, for example, Cheson B. D. and J. P. Leonard, *N. Engl. J. Med.*, 359(6):613-626 (2008)). Preferably, in any subjects receiving any of the pan-B-cell immunoablative therapies (e.g., Rituxan, Bexxar, Zevalin), any booster administrations of the autologous idiotype vaccine are administered at least about one month after such immunoablative therapies, as it typically takes approximately 14-21 days for B-cell recovery.

In some embodiments of the present invention, an antibody is a monoclonal antibody that specifically binds CD-20 on a B-cell. In other embodiments, an antibody is a monoclonal antibody that specifically binds CD-22 on a B-cell. However, without wishing to be bound by theory, it is contemplated that a human or humanized monoclonal antibody that selectively binds any one of B-cell specific antigens CD3d, CD5, CD6, CD9, CD19, CD20, CD21, CD22, CD23, CD24, CD27, CD28, CD37, CD38, CD40, CD45, CD46, CD48, CD52, CD53, CD69, CD70, CD72, CD73, CD74, CD79a, CD79b, CD80, CD81, CD83, CD85a, CD85d, CD85e, CD85h, CD85i, CD85j, CD85k, CD86, CD96, CD98, CD100, CD121b, CD124, CD127, CD132, CD150, CD152, CD154, CD157, CD166, CD169, CD179a, CD179b, CD180, CD185, CD196, CD197, CD205, CDw210a, CD213a1, CD257, CD267, CD268, CD269, CD274, CD275, CD276, CD278, CD279, CD300a, CD300c, CD307, CD314, CD316, CD317, CD319, CD320, CDw327, CD331, Death receptor, or HLA-DR may be used in the methods of the invention.

Commercially available monoclonal antibodies that specifically bind B-cell specific antigens include, for example, rituximab, which binds CD-20, and epratuzumab, which binds CD-22 (see, for example, Cheson B. D. and J. P. Leonard, *N. Engl. J. Med.*, 359(6):613-626 (2008)).

Antibodies or antigen-binding portions thereof can be tested for binding to a B-cell or a B-cell specific antigen by, for example, standard assays known in the art, such as ELISA, FACS analysis and/or Biacore analysis.

Antibodies or antigen-binding portions useful in the methods of the invention may be labeled with a detectable substance using well known techniques. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{14}C$, $^{123}I$, $^{124}I$, $^{125}I$, $^{131}O$, $^{99m}Tc$, $^{35}S$ or $^{3}H$.

Modes of Administration

The various compounds used in the methods described herein may be administered orally, parenterally (e.g., intravenously), intramuscularly, sublingually, buccally, rectally, intranasally, intrabronchially, intrapulmonarily, intraperitoneally, topically, transdermally and subcutaneously, for example. The amount of compound administered in a single dose may dependent on the subject being treated, the subject's weight, the manner of administration and the judgment of the prescribing physician. Generally, however, administration and dosage and the duration of time for which a composition is administered will approximate that which are necessary to achieve a desired result.

In general, a therapeutically effective amount of a monoclonal antibody such as, for example, an antibody that specifically binds CD-20 or CD-22, from about 0.0001 mg/Kg to 0.001 mg/Kg; 0.001 mg/kg to about 10 mg/kg body weight or from about 0.02 mg/kg to about 5 mg/kg body weight. In some embodiments, a therapeutically effective amount of a monoclonal antibody is from about 0.001 mg to about 0.01 mg, about 0.01 mg to about 100 mg, or from about 100 mg to about 1000 mg, for example.

In some embodiments, a therapeutically effective amount of an autologous idiotype vaccine is from about 0.001 mg to about 0.01 mg, about 0.01 mg to about 100 mg, or from about 100 mg to about 1000 mg, for example. In some embodiments, an effective amount of the autologous idiotype vaccine is one or more doses of 0.5 mg.

In some embodiments, an effective amount of an antibody administered to a subject having non-Hodgkin's lymphoma, Hodgkin's lymphoma, chronic lymphocytic leukemia or multiple myeloma between about 100 mg/m$^2$ and 200 mg/m$^2$, or between about 200 mg/m$^2$ and 300 mg/m$^2$ or between about 300 mg/m$^2$ and 400 mg/m$^2$. In a particular embodiment, an effective amount of a monoclonal antibody that selectively binds a B-cell specific antigen is about 375 mg/m$^2$.

The optimal pharmaceutical formulations for a desired monoclonal antibody can be readily determined by one or ordinary skilled in the art depending upon the route of administration and desired dosage. (See, for example, Remington's Pharmaceutical Sciences, 18th Ed. (1990), Mack Publishing Co., Easton, Pa., the entire disclosure of which is hereby incorporated by reference).

Antibodies for use in the methods or compositions described herein can be formulated for the most effective route of administration, including for example, oral, transdermal, sublingual, buccal, parenteral, rectal, intranasal, intrabronchial or intrapulmonary administration.

In some embodiments, the vaccine compositions used in the methods of the present invention include one or more cytokines such as, for example, GM-CSF. GM-CSF is a potent immunostimulatory cytokine with efficacy in promoting anti-tumor response, particularly T cell responses. In general, however, any cytokine or chemokine that induces inflammatory responses, recruits antigen presenting cells (APC) to the tumor and, possibly, promotes targeting of antigen presenting cells (APC) may be used in the vaccine compositions.

The autologous idiotype vaccines useful in the methods of the present invention may be administered by any conventional route including oral and parenteral. Examples of parenteral routes are subcutaneous, intradermal, transcutaneous, intravenous, intramuscular, intraorbital, intracapsular, intrathecal, intraspinal, intracisternal, intraperitoneal, etc. Preferably, the primary treatment and one or more booster doses of the autologous idiotype vaccine are administered by the same route, e.g., subcutaneously.

An effective amount of a vaccine composition administered to a subject will vary from individual to individual and can be, for example, between about 0.01 µg/kg and about 1 mg/kg body weight. The amount of the immunogen per dose can range from about 0.01 mg to 100 mg of protein per subject per injection.

Administration of the immunogenic (vaccine) composition is preferably by injection on one or multiple occasions to produce systemic immunity. In general, multiple administrations of the vaccine in a standard immunization protocol are used, as is standard in the art. For example, the vaccines can be administered at approximately two to six week intervals, or monthly, for a period of from one to six inoculations in order to provide protection. The vaccine may be administered by any conventional route including oral and parenteral. Examples of parenteral routes are subcutaneous, intradermal, transcutaneous, intravenous, intramuscular, intraorbital, intracapsular, intrathecal, intraspinal, intracisternal, intraperitoneal, etc.

Without wishing to be bound by theory, it is contemplated that vaccination may result in a systemic immune response, which includes either or both of an antibody response and a cell-mediated immune response, which will provide an anti-cancer therapeutic effect and/or result in antibodies and activated T lymphocytes of various classes which may be used themselves as therapeutic agents, for example, for producing passive immunity in cancer-bearing subjects.

The vaccine compositions used in the methods of the present invention may further include one or more adjuvants or immunostimulatory agents. Examples of adjuvants and immunostimulatory agents include, but are not limited to, GM-CSF, aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, whole organisms or subcellular fractions of the bacteria *Propionobacterium acnes* or *Bordetella pertussis*, polyribonucleotides, sodium alginate, lanolin, lysolecithin, vitamin A, saponin and saponin derivatives, liposomes, levamisole, DEAE-dextran, blocked copolymers or other synthetic adjuvants. Such adjuvants are readily commercially available.

Depending on the intended mode of administration, the compounds used in the methods described herein (e.g., autologous idiotype vaccines) may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. Each dose may include an effective amount of a compound used in the methods described herein in combination with a pharmaceutically acceptable carrier and, in addition, may include other medicinal agents, pharmaceutical agents, carriers, adjuvants, diluents, etc.

Liquid pharmaceutically administrable compositions can prepared, for example, by dissolving, dispersing, etc., a compound for use in the methods described herein and optional pharmaceutical adjuvants in an excipient, such as, for example, water, saline aqueous dextrose, glycerol, ethanol, and the like, to thereby form a solution or suspension. For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; see, for example, Remington's Pharmaceutical Sciences, 18th Ed. (1990), Mack Publishing Co., Easton, Pa., the entire disclosure of which is hereby incorporated by reference).

Methods of Treatment

Methods of treatment described herein encompass methods of eliminating or substantially reducing a B-cell derived malignancy such as, for example, non-Hodgkin's lymphoma, Hodgkin's lymphoma, chronic lymphocytic leukemia, mantle cell lymphoma and multiple myeloma.

In some embodiments, the B-cell derived malignancy to be treated is selected from among non-Hodgkin's lymphoma, chronic lymphocytic leukemia (CLL), small lymphocytic lymphoma, multiple myeloma, mantle cell lymphoma, B-cell prolymphocytic leukemia, lymphoplasmocytic lymphoma, splenic marginal zone lymphoma, marginal zone lymphoma (extra-nodal and nodal), follicular lymphoma (grades I, II, III, or IV), diffuse large B-cell lymphoma, mediastinal (thymic) large B-cell lymphoma, intravascular large B-cell lymphoma, primary effusion lymphoma, and Burkitt lymphoma/leukemia.

A subject having non-Hodgkin's lymphoma, Hodgkin's lymphoma, chronic lymphocytic leukemia, mantle cell lymphoma or multiple myeloma can be diagnosed using standard techniques known in the art. For example, a diagnosis may be made by removing a part of a lymph node and examining the cells under a microscope. Biopsies may also be taken from other body tissues.

Subsequent to diagnosis, a subject having non-Hodgkin's lymphoma, Hodgkin's lymphoma, chronic lymphocytic leukemia, mantle cell lymphoma or multiple myeloma can be treated using methods of the invention.

In some embodiments, a subject having non-Hodgkin's lymphoma or Hodgkin's lymphoma or chronic lymphocytic leukemia, mantle cell lymphoma or multiple myeloma is administered an effective amount of an autologous idiotype vaccine, which may optionally be administered in conjunction with an effective amount of GM-CSF, followed by re-administration of the autologous anti-idiotype vaccine one or more times as a booster.

In some embodiments, a subject having non-Hodgkin's lymphoma or Hodgkin's lymphoma or chronic lymphocytic leukemia or mantle cell lymphoma or multiple myeloma is administered an autologous idiotype vaccine (optionally in conjunction with GM-CSF) and an effective amount of a monoclonal antibody which specifically binds a B-cell specific antigen, e.g., CD-20 or CD-22, followed by re-administration of the autologous anti-idiotype vaccine, without the monoclonal antibody, as a booster.

In some embodiments, a booster dose(s) of the autologous idiotype vaccine is administered at least about 20 months after the initial treatment (i.e., at least 20 months after last vaccination). In some embodiments, the booster dose(s) of the autologous idiotype vaccine is administered to the subject about 24 months to about 30 months after completion of the initial treatment (i.e., after last vaccination). In some embodiments, the booster doses of the autologous idiotype vaccine are administered to the subject about 24 months to about 30 months after completion of the initial treatment and administered again in about 12 to about 18 months thereafter. In some embodiments, the booster doses of the autologous idiotype vaccine are administered to the subject about 24 months to about 30 months after completion of the initial treatment and administered again in about 12 to about 18 months thereafter, and periodically at about every 12 to 18 months thereafter.

The initial treatment with the autologous idiotype vaccine can comprise one or more administrations. Preferably, the initial treatment is a regimen comprising a plurality of administrations of the autologous idiotype vaccine. In some embodiments, the initial treatment comprises five administrations of the autologous idiotype vaccine over a period of about 6 months. In some embodiments, the autologous idiotype vaccine comprises an antigen associated with a B-cell derived malignancy in the subject, and a carrier molecule linked to the antigen, and the initial treatment comprises administration (e.g., subcutaneous) of 0.01 mg to about 100 mg of the autologous idiotype vaccine (day 1) and about 50 $\mu g/m^2$/day to about 200 $\mu g/m^2$/day granulocyte monocyte-colony stimulating factor (days 1-4) at about 1, 2, 3, 4, and 6 months. In some embodiments, the autologous idiotype vaccine comprises an antigen associated with a B-cell derived malignancy in the subject, and keyhole limpet hemocyanin linked to the antigen, and the initial treatment comprises administration (e.g., subcutaneous) of 0.5 mg of the autologous idiotype vaccine (day 1) and 100 $\mu g/m^2$/day granulocyte monocyte-colony stimulating factor (days 1-4) at about 1, 2, 3, 4, and 6 months.

In some embodiments, the booster dose comprises about 0.01 mg to about 100 mg autologous idiotype vaccine per administration (e.g., subcutaneous). In some embodiments, the booster dose comprises about 0.5 mg autologous idiotype vaccine per administration (e.g., subcutaneous).

In some embodiments, the subject has undergone a different therapy (i.e., other than the autologous idiotype vaccine therapy) prior to the initial treatment, such as chemotherapy and/or immunotherapy. In some embodiments, the different therapy comprises therapy with a monoclonal antibody, such as rituximab, tositumomab, ibritumomab tiuxetan, or epratuzumab (see, for example, Cheson B. D. and J. P. Leonard, *N. Engl. J. Med.*, 359(6):613-626 (2008)). In some embodiments, the different therapy comprises a radioimmunotherapy, such as ibritumomab tiuxetan. In some embodiments, the different therapy comprises a regimen of PACE (prednisone, doxorubicin, cyclophosphamide, and etoposide) or CHOP-R (cyclophosphamide, hydroxydaunrubicin, oncovin, prednisone/prednisolone, and rituximab). Preferably, the different therapy induces complete remission in the subject prior to the initial treatment with the vaccine. In some embodiments, the subject is in complete remission at the time of the initial treatment with the vaccine. In some embodiments, the subject is in complete remission at the time that each of the one or more booster doses is administered.

Endogenous mechanisms for controlling autoimmune responses (natural tolerance) and of inducing tolerance (adaptive tolerance) exist. T-regulatory lymphocytes (T-regulatory cells or T-regs) are a specialized subset of $CD4^+$ T cells implicated in the suppression of immune response, fulfilling an important role in the maintenance of immune homeostasis (Sakaguchi S. "Regulatory T cells: key controllers of immunologic self-tolerance," *Cell*, 101:455-458 (2000)). T-regs differ from other $CD4^+$ cells in expressing high levels of CD25 and by expression of the forkhead/winged helix transcription factor (Foxp3). Under some circumstances, it may be desirable to inhibit T-reg cell activity and/or reduce the number of T-regs in a subject (i.e., to inhibit the immunosuppressive effects of T-regs) prior to vaccinating the subject with an autologous idiotype vaccine. Accordingly, in some embodiments of the invention, the subject has reduced T-regulatory cell activity and/or reduced numbers of T-regulatory cells at the time of administration of an idiotype vaccine. Reduced T-regulatory cell activity and/or reduced T-regulatory cell numbers may be achieved in a subject by administering an inhibitor of T-regulatory cells to the subject. The reduced T-regulatory cell activity and/or reduced numbers of T-regulatory cells can be relative to the normal activity and/or cell numbers in the subject and/or relative to a normal control population, for example. The normal T-reg level may be one which is consistent with an immunosuppressive state in the subject. As used herein, the term "T-reg level" refers to T-reg cell activity, T-reg cell number, or both.

Agents capable of inhibiting T-reg immunosuppressive activity and/or Treg numbers, and which may be utilized in the invention, are known (Cohen A. D. et al., "Agonist anti-GITR antibody enhances vaccine-induced CD8(+) T-cell responses and tumor immunity", *Cancer Res* 66:4904-49-12 (2006); Onizuka S. et al., "Tumor rejection by in vivo administration of anti-CD25 (interleukin-2 receptor alpha) monoclonal antibody" *Cancer Res*, 59:3128-3133 (1999); Shimizu J. et al., "Induction of tumor immunity by removing CD25+CD4+ T cells: a common basis between tumor immunity and autoimmunity," *J. Immunol.*, 163:5211-5218 (1999); Tanaka H. et al., "Depletion of CD4+ CD25+ regulatory cells augments the generation of specific immune T cells in tumor-draining lymph nodes," *J. Immunother.*, 25:207-217 (2002); Ko K. et al., "Treatment of advanced tumors with agonistic anti-GITR mAB and its effects on tumor-infiltrating Foxp3+CD25+CD4+ regulatory T cells," *J. Exp. Med.*, 202:885-891 (2005); Ghiringhelli F. et al., "CD4+CD25+ regulatory T cells suppress tumor immunity but are sensitive to cyclophosphamide which allows immunotherapy of established tumors to be curative," *Eur. J. Immunol.*, 34:336-344 (2004); Galustian C. et al., "The anti-cancer agents lenalidomide and pomalidomide inhibit proliferation and function of T regulatory cells" *Cancer Immunol Immunother.*, 58(7):1033-1045 (2009); Houot R. et al., "T-cell modulation combined with intratumoral CpG cures lymphoma in a mouse model without the need for chemotherapy", *Blood*, 113(15):3546-3552 (2009); Nizar S. et al., "T-regulatory cell modulation: the future of cancer immunotherapy?", *British Journal of Cancer*, 100:1697-1703; and Dias de Rezende, L. C. et al., "Regulatory T cell as a target for cancer therapy", *Arch. Immunol. Ther. Exp.*, 58:179-190 (2010)).

Examples of Treg inhibitors include, but are not limited to, lenalidomide, pomalidomide, oxazaphosphorines such as cyclophosphamide, anti-CD25 monoclonal antibody, IL-2Rα monoclonal antibody, and anti-glucocorticoid-induced tumor necrosis factor receptor (anti-GITR) monoclonal antibody. In some embodiments, the inhibitor of T-regulatory cells reduces the activity and/or reduces the number of $CD4^+CD25_{Hi}FoxP3^+$ natural T-regulatory cells in the subject. In some embodiments, the methods of the invention comprise administering a T-regulatory cell inhibitor to the subject, and subsequently administering an idiotype vaccine to the subject (e.g., an idiotype vaccine comprising an autologous idiotype immunoglobulin comprising at least an IgM constant region).

The T-reg cell level can be determined by obtaining one or more biological samples from the subject (for example, blood, peripheral blood, synovial fluid, or other biological tissue or fluid that may be sampled and in which T-reg cells are found) and determining the T-reg cell level in the sample(s) prior to administration of a vaccine of the invention. Ideally, the immunosuppressive effect of T-reg cells in the subject is inhibited or reduced to maximize the clinical effectiveness of the subsequently administered vaccine. Thus, preferably, the T-reg cell inhibitor is administered to the subject until the T-reg cell level in the subject is below that of a threshold, immunosuppressive T-reg cell level. In some embodiments, the T-reg cell level is determined two or more times and the T-reg cell inhibitor is administered to the subject until the T-reg cell level in the subject is below that of a threshold, immunosuppressive T-reg cell level, prior to administration of the vaccine. T-reg cell level can be determined by methods known in the art. For example, T-reg cells in a sample can be quantified by flow cytometry. Subpopulations of T-reg cells can be targeted for level determination, such as CD4+ CD25HIFoxp3+ cells.

In methods of the invention, determining T-reg cell level in a subject may involve comparing the observed level to that of a reference T-reg cell level or suitable control (for example, to assess whether T-reg cell level is below, equal to, or above a threshold level, e.g., a "normal" level). A "suitable control" is a predetermined value associated with T-reg cell level useful for comparison purposes, which can take many different forms. Exemplary forms include, but are not limited to, for example, T-reg cell numbers, a transcription rate, mRNA level, translation rate, protein level, protein structure, biological activity, cellular characteristic or property, genotype, phenotype, enzymatic activity etc. associated with T-reg cells. In some embodiments, a "suitable control" is a predetermined T-reg cell activity, which is compared to T-reg cell activity in a sample obtained from a subject being identified as suitable or not suitable for treatment with a vaccine of the invention. In other embodiments, a "suitable control" is a predetermined T-reg cell number, which is compared to T-reg cell number in a sample obtained from a subject being identified as suitable or not suitable for treatment with a vaccine of the invention. In other embodiments, a "suitable control" is a predetermined T-reg cell number and activity, which is compared to T-reg cell number and activity in a sample obtained from a subject being identified as suitable or not suitable for treatment with a vaccine of the invention. In other embodiments, a "suitable control" is a predetermined T-reg cell level, which is compared to a T-reg cell level in a sample obtained from a subject in which a clinical measure was achieved, for example an T-reg cell level obtained from cells in a subject who reached or failed to reach a desired immune response.

In some embodiments, a "suitable control" can be a single cut-off value, such as a median or mean. A single cut-off value can be established, for example, based upon comparative groups, such as in groups having a T-reg level which reduces a desirable immune response to a vaccine of the invention and/or which interferes or impedes a desired clinical outcome following treatment with a vaccine of the invention. For example, samples can be derived from various individuals or blood banks and a T-reg cell level can be measured in each sample prior to being subjected to treatment with a vaccine of the invention. Consequently, a single cut-off value can be based on the mean of T-reg cell number and/or activity in samples which are immunosuppressive to an extent that reduces a desirable immune response to a vaccine of the invention and/or which interferes or impedes a desired clinical outcome following treatment with a vaccine of the invention. Another comparative group can be, for example, a T-reg cell level in a group of individuals with a family history of successful treatment with a vaccine of the invention and a group without such a family history. Another comparative group can be, for example, a T-reg cell level in a group of individuals with a history of treatment with a vaccine of the invention having achieved maximal immune response and/or clinical outcome and a group having not achieved maximal immune response and/or clinical outcome.

In some embodiments of the methods of the present invention, a subject is identified as being suitable for vaccine treatment if the T-reg cell level measured in a sample (for example, blood sample) obtained from the subject is consistent with an "suitable control." By "consistent with a suitable control," is meant that the T-reg cell level is either equal to or below a predetermined T-reg cell level control, in case of a single cut-off value, or the T-reg cell level falls within a range for a predetermined T-reg cell level control. In some embodiments, a subject is identified as being suitable for vaccine treatment if the T-reg cell level in a sample from the subject is consistent with a maximal immune response (non-immune suppressed). By "consistent with a maximal immune response," is meant that the T-reg cell level is either equal to or lower than a predetermined "immunosuppressive level," in case of a single cut-off value, or the T-reg cell level falls within a range for a predetermined immunosuppressive level. In this way, it can be determined whether a subject is suitable for vaccine treatment (e.g., the T-reg cell level in a sample from the subject is consistent with a maximal immune response or "non-immune suppressed") or whether the subject should be administered a T-reg cell inhibitor (e.g., the T-reg cell level in a sample from the subject is inconsistent with or below a maximal immune response or "immune suppressed").

Assessing Immune Response

The methods of the invention may further comprise assessing whether an immune response to the autologous idiotype vaccine has been elicited in the subject and, optionally, determining whether the immune response against the vaccine has subsequently diminished (e.g., in character and/or extent). Optionally, the methods can include administering at least one booster dose of the autologous idiotype vaccine to the subject if the immune response against the vaccine is determined to have diminished.

An assessment can be made of the nature and/or extent of the subject's immune response to the vaccine (e.g., cellular and/or humoral response) one or more times after the initial treatment with the vaccine. Preferably, an assessment of the subject's immune response is also made before the subject's initial treatment with the autologous anti-idiotype vaccine (e.g., to establish a control or base-line for comparison to a subsequent assessment or assessments post-treatment). The subject's immune response to the vaccine can also be monitored by making an assessment before and after each booster dose is given. The timing and frequency of booster doses can be at the physician's discretion, and/or can be dependent on the results of assessments of the subject's immune response to the vaccine. For example, if the immune response is considered to be diminished (e.g., reduced or impaired in character and/or extent) following one of these assessments (e.g., either through loss of antibody response and/or a reduction of tumor-reactive T-cells or cytokines), it would indicate that the subject lost some of the immune response against the B-cell idiotype and therefore lost some anti-tumor immunity induced by the first cycle of vaccination. The physician could therefore consider administering a booster dose (e.g., one or more booster injections) or series of booster doses to the subject.

When assessing the subject's immune response, the immune response against the B-cell idiotype is preferably assessed. However, the assessment can include an assessment of the subject's immune response against any component of the vaccine. For example, an assessment of the subject's immune response against the anti-idiotype, or against a carrier molecule (e.g., KLH), or against both, can be made.

In some embodiments, enzyme-linked immunosorbent assays (ELISA) and/or T-cell proliferation assays are performed for detection of anti-Id humoral and/or cellular responses after vaccination (Hsu F. J. et al., "Tumor-specific idiotype vaccines in the treatment of patients with B-cell lymphoma—long term results of a clinical study," *Blood*, 1997, 89:3129-3135).

The subject's immune response can be monitored by making multiple assessments after the initial treatment at uniform time intervals (e.g., every three months, every six months, every nine months, or annually) or at non-uniform time intervals. Monitoring of the subject's immune response to the vaccine can continue for a pre-determined period of time, for a time determined based on therapeutic outcome, or indefinitely. Preferably, the subject's immune response is monitored from a time period starting prior to initial vaccination and continuing for a period of at least five years, or indefinitely.

Typically, each assessment will involve obtaining an appropriate biological sample from the subject. The appropriate biological sample will depend upon the particular aspect of the subject's immune response to be assessed (e.g., depending upon the particular assay). For example, in some embodiments, the biological sample will be one or more specimens selected from among blood, peripheral blood mononuclear cells (PBMC), and B-cell derived tumor. Samples for assessments are taken at a time point appropriate to obtain information regarding the immune response at the time of interest. For example, a sample may be taken from the subject from a time prior to vaccination and additional samples may be taken from the subject periodically after vaccination to determine the nature and extent of the immune responses observed.

In some embodiments, assessment of the immune response includes assessment of one or more of the following aspects of the immune response: anti-idiotype (anti-Id) humoral responses; B-cell derived tumor-specific antibodies; tumor-reactive T-cell precursor frequencies (e.g., via an IFN-gamma response); biomarkers in the B-cell derived tumor that correlate with clinical outcome following autologous anti-idiotype vaccine therapy; and B-cell derived tumor-specific CD4+ and CD8+ T-cell responses.

Preferably, the immune response is assessed by conducting one or more humoral response assays and/or cellular response assays, such as those described by Neelapu et al. (*Nature Medicine*, 11(9):986-991 (2005)), which is incorporated herein by reference in its entirety. Peripheral blood B and T cells can be collected from the subject and blood counts can be determined, including but not limited to CD3-CD19+ B cells, CD3+CD4+ T cells, and CD3+CD8+ T cells. Tumor cells can be determined, and PBMCs isolated. Both B-cells and tumor cells can be activated with recombinant CD40 ligand trimer, as described in Neelapu et al. (2005). Depending on the type of immune response to be assessed (e.g., humoral, cellular, or both), one or more of the following assays may be used:

Humoral immune response assay: to assess anti-Id humoral responses and tumor-specific antibodies (see, for example, Kwak et al., *Lancet*, 345:1016-1020 (1995), which is incorporated herein by reference in its entirety).

IFN-gamma ELISPOT assay: to assess tumor-reactive T-cell precursor frequencies via an IFN-gamma response (see, for example, Malyguine et al., *J. Trans. Med.*, 2:9 (2004) and Neelapu et al., *Clin. Cancer Res.*, 10:8309-8317 (2004), which are each incorporated herein by reference in its entirety).

Cytokine induction assay: to assess biomarkers in the tumor that correlate with clinical outcome following autologous anti-idiotype vaccine therapy (see, for example, Neelapu et al. (2004)).

Intracellular cytokine assay: to assess tumor-specific CD4+ and CD8+ T-cell responses (Neealapu et al., *J. Cancer Res. Clin. Oncol.*, 127 Suppl. 2, R14-19 (2001)).

Assays such as those listed above (either individually or in combination) can be used to periodically monitor (e.g., every 3, 6 months to 1 year) after a patient receives a course of the autologous idiotype vaccine, and may be used to determine an optimal schedule of booster vaccinations. In that case, if the immune response is considered to be reduced or impaired following one of these periodic tests (e.g., either through loss of antibody response and/or a reduction of tumor-reactive T-cells or cytokines), then the subject would be considered to have lost some of the anti-tumor immunity induced by the first cycle of vaccination. The physician could therefore consider administering a booster injection or series of injections to the subject.

Experimental controls are considered fundamental in experiments designed in accordance with the scientific method. It is routine in the art to use experimental controls in scientific experiments to prevent factors other than those being studied from affecting the outcome.

Exemplified Embodiments

The following are exemplified embodiments:

1. A method for selecting an idiotype vaccine for treatment of a B-cell derived malignancy in a subject, comprising:

(a) obtaining isolated nucleic acid from a cell sample comprising one or more cells of the B-cell derived malignancy (the "tumor cell sample");

(b) amplifying at least a portion of the genomic region of the one or more cells that is characteristic of the tumor cell sample (the "tumor identifying region"), resulting in amplicons that collectively span the tumor identifying region (the "tumor cell sample amplicons");

(c) sequencing the tumor cell sample amplicons, resulting in reads (the "tumor cell sample reads") that are a quantity of sequences representative of the nucleic acid sequences of the tumor identifying region present in the tumor cell sample;

(d) optionally, aligning the tumor cell sample reads to reference sequences (or to the potential idiotype-secreting clones (e.g., hybridoma) if using VDJ spanning primers);

(e) producing a plurality of clones from the tumor cell sample ("potential idiotype-secreting clones"), wherein each clone is representative of one clonal population of B-cells harboring the tumor identifying region common to one clonal population of B-cells;

(f) isolating nucleic acid from one or more of the potential idiotype-secreting clones ("potential idiotype secreting clones nucleic acid sample");

(g) amplifying at least a portion of the tumor identifying region of the potential idiotype secreting clones nucleic acid sample, resulting in amplicons that collectively span the tumor identifying region ("the potential idiotype secreting clone amplicon pool");

(h) sequencing the amplicons of the potential idiotype secreting clone amplicon pool, wherein the resulting reads ("potential idiotype secreting clone reads") are a quantity of sequences representative of the nucleic acid sequences of the tumor identifying region present in the tumor cell sample;

(i) optionally, aligning the tumor cell sample reads to reference sequences;

(j) determining a quantity of each sequence read from the tumor cell sample reads;

(k) aligning the potential idiotype secreting clone reads with the most abundant tumor cell sample reads (the number of unique sequences which comprise, e.g., greater than about 10% of the tumor cell sample reads); and (l) selecting one or more potential idiotype secreting clones from the plurality of potential idiotype secreting clones, wherein the selected clone(s) has the same or substantially similar tumor identifying region (e.g., greater than about 80% sequence identity) as the most abundant tumor cell sample reads.

2. The method of embodiment 1, further comprising: (m) preparing an idiotype vaccine for treatment of the B-cell derived malignancy, wherein the vaccine comprises an idiotype immunoglobulin from the selected clone(s) having the same or substantially similar tumor identifying region as the most abundant tumor cell sample reads.

3. The method of embodiment 1, further comprising administering the idiotype vaccine to the subject.

4. The method of embodiment 1, wherein preparing the idiotype vaccine further comprises conjugating the idiotype immunoglobulin with an immunogenic carrier molecule.

5. The method of embodiment 4, wherein the immunogenic carrier molecules comprises keyhole limpet hemocyanin (KLH).

6. The method of embodiment 3, further comprising administering an effective amount of an adjuvant to the subject.

7. The method of embodiment 6, wherein the adjuvant comprises granulocyte monocyte-colony stimulating factor (GM-CSF).

8. The method of embodiment 3, wherein the B-cell derived malignancy is in complete remission at the time of said administering.

9. The method of embodiment 1, wherein the isolated nucleic acid of (a) comprises genomic DNA.

10. The method of embodiment 1, wherein the isolated nucleic acid of (a) comprises RNA.

11. The method of embodiment 1, further comprising isolating the nucleic acid from the cell sample prior to step (a).

12. The method of embodiment 1, further comprising obtaining the cell sample from the subject and isolating the nucleic acid from the cell sample prior to step (a).

13. The method of embodiment 1, wherein the cell sample is a sample of blood, bone marrow, or lymph node.

14. The method of embodiment 1, wherein the tumor identifying region of step (b) comprises complementarity determining region 3 (CDR3) of the immunoglobulin heavy chain (IgH) gene.

15. The method of embodiment 1, wherein the tumor identifying region of step (b) comprises:
    (a) a rearranged VDJ region of the immunoglobulin heavy chain (IgH) gene; or
    (b) a rearranged VJ region of the immunoglobulin kappa (IgK) gene; or
    (c) a rearranged VJ region of the immunoglobulin lambda (IgL) gene.

16. The method of embodiment 1, wherein the tumor identifying region of step (b) is a translocation region associated with the B-cell derived malignancy.

17. The method of embodiment 16, wherein the translocation region comprises:
    (a) a bcl-1/IgH fusion sequence, wherein the B-cell derived malignancy is mantle cell lymphoma (MCL); or
    (b) a bcl-2/IgH fusion sequence, wherein the B-cell derived malignancy is follicular lymphoma; or
    (c) a bcl-3/IgH fusion sequence, wherein the B-cell derived malignancy is B-cell chronic lymphocytic leukemia (CLL); or
    (d) a bcl-6/IgH fusion sequence, wherein the B-cell derived malignancy is diffuse large cell lymphoma (DLCL); or
    (e) a fibroblast growth factor receptor (FGFR)/IgH fusion sequence, wherein the B-cell derived malignancy is multiple myeloma; or
    (f) a cyclin D1 sequence, wherein the B-cell derived malignancy is multiple myeloma; or
    (g) a c-myc/IgH fusion sequence, wherein the B-cell derived malignancy is Burkitt's lymphoma; or
    (h) a bcl-6/IgL fusion sequence, wherein the B-cell derived malignancy is diffuse large cell lymphoma (DLCL); or
    (i) a bcl-6 or CD95 fusion sequence (a.k.a. FAS or APO1) sequence; wherein the B-cell derived malignancy is Non-Hodgkin's lymphoma (NHL); or
    (j) a Pax-5, c-myc, Pim-1, or Rho/TTF sequence; wherein the B-cell derived malignancy is DLCL; or
    (k) a bcl-6, Pax-5, c-myc, Pim-1, Rho/TTF sequence; wherein the B-cell derived malignancy is NHL.

18. The method of embodiment 1, wherein the tumor identifying region comprises a unique genetic element.

19. The method of embodiment 18, wherein the unique genetic element is selected from among a translocation, single nucleotide polymorphism (SNP), or somatic mutation.

20. The method of embodiment 18 or 19, wherein the method further comprises sequencing the nucleic acid of the tumor sample entirely using whole genome sequencing or exome sequencing; and aligning the determined nucleic acid sequences with reference sequences to identify the unique genetic elements of the one or more cells of the tumor cell sample.

21. The method of embodiment 1, wherein the tumor identifying region of step (b) comprises a rearranged VDJ region of the immunoglobulin heavy chain (IgH) gene, and wherein said amplifying of step (b) comprises amplifying DNA between primers that target the framework region (FR1, FR2, and/or FR3) and joining (J) region of the IgH variable gene of the one or more cells.

22. The method of embodiment 21, wherein said amplifying of step (b) is carried out using 7 forward primers for the FR2 region (to account for the 7 common family members of the FR2 region) and 1 consensus primer for the IgH J segment.

23. The method of embodiment 1, wherein the sequencing step of (c) comprises high-throughput sequencing (HTS).

24. The method of embodiment 23, wherein the HTS is selected from among pyrosequencing, semiconductor sequencing, or sequencing by synthesis (SBS).

25. The method of embodiment 23 or 24, wherein the HTS generates a target of at least 15,000 reads per sample.

26. The method of embodiment 23 or 24, wherein the tumor identifying region of step (b) comprises a rearranged VDJ region of the immunoglobulin heavy chain (IgH) gene, and wherein the tumor cell sample reads are a quantity of sequences representative of the nucleic acid sequences of the VDJ region present in the tumor cell sample.

27. The method of embodiment 1, wherein the reference sequences in (d) are sequences in one or more publicly available databases (e.g., using the National Center for Biotechnology Information's (NCBI's) Basic Local Alignment Search Tool (BLAST)).

28. The method of embodiment 27, wherein the tumor identifying region of (b) comprises a rearranged VDJ region of the immunoglobulin heavy chain (IgH) gene, and wherein said aligning of (d) further comprises assigning a V, D, and J allele to tumor cell sample amplicons by aligning the tumor cell sample amplicons with nucleotide sequences from publicly available databases (e.g., using the National Center for Biotechnology Information's (NCBI's) Basic Local Alignment Search Tool (BLAST), immunoglobulin BLAST (Ig-BLAST), the International ImMunoGene Tics (IMGT) database, iHMMune-align alignment tool).

29. The method of embodiment 27, wherein the tumor cell sample amplicons are aligned to reference sequences using a Smith-Waterman algorithm or a hidden Markov-based alignment.

30. The method of embodiment 1, further comprising performing a quality control step on the tumor cell sample reads of (c).

31. The method of embodiment 30, wherein the quality control step comprises: eliminating any tumor cell sample reads of (c) that are the result of sequence artifact; and/or assigning a quality score to each tumor cell sample read of (c), comparing each assigned quality score to a reference threshold quality score, and replacing or annotating any nucleotides in each tumor cell sample amplicon designated not to have achieved the threshold quality score.

32. The method of embodiment 1, wherein the potential idiotype-secreting clones of (e) are produced by hybridoma rescue fusion hybridization.

33. The method of embodiment 32, wherein the hybridoma is produced by fusion of a malignant B-cell obtained from the subject and a murine/human heterohybridoma myeloma cell.

34. The method of embodiment 33, wherein the murine/human heterohybridoma myeloma cell is the K6H6/B5 cell line.

35. The method of embodiment 1, wherein the potential idiotype-secreting clones of (e) are produced using a method other than hybridoma rescue fusion hybridization.

36. The method of embodiment 35, wherein the potential idiotype-secreting clones of (e) are produced recombinantly by introducing a genetic construct into a host cell.

37. The method of embodiment 1, wherein the amplification step of (g) is performed in a multiplex manner by polymerase chain reaction (PCR) using barcoded primers, wherein each unique barcode corresponds to one amplicon from one potential idiotype-secreting clone.

38. The method of embodiment 37, wherein the sequencing step of (h) is carried out in a multiplexed manner, wherein all the amplicons of the potential idiotype secreting clone amplicon pool are sequenced simultaneously, and wherein each barcode identifies the amplicon corresponding to each potential idiotype secreting clone.

39. The method of embodiment 38, wherein the potential idiotype secreting clone amplicon pool consists of one or more potential idiotype-secreting clones from one subject.

40. The method of embodiment 38, wherein the potential idiotype secreting clone amplicon pool consists of one or more potential idiotype-secreting clones from a plurality of subjects.

41. The method of embodiment 1, wherein the sequencing step of (h) comprises high-throughput sequencing (HTS).

42. The method of embodiment 41, wherein the HTS is selected from among pyrosequencing, semiconductor sequencing, or sequencing by synthesis (SBS).

43. The method of embodiment 41, wherein the HTS generates a target of at least 15,000 reads per sample.

44. The method of embodiment 41, wherein the tumor identifying region of step (b) comprises a rearranged VDJ region of the immunoglobulin heavy chain (IgH) gene, and wherein the potential idiotype secreting clone reads are a quantity of sequences representative of the nucleic acid sequences of the VDJ region present in the tumor cell sample.

45. The method of embodiment 1, further comprising performing a quality control step on the potential idiotype secreting clone reads of (h).

46. The method of embodiment 45, wherein the quality control step comprises: eliminating any potential idiotype secreting clone reads of (h) that are the result of sequence artifact; and/or assigning a quality score to each potential idiotype secreting clone read of (h), comparing each assigned quality score to a reference threshold quality score, and replacing or annotating any nucleotides in each potential idiotype secreting clone amplicon designated not to have achieved the threshold quality score.

47. The method of embodiment 1, wherein the selecting step of (l) comprises selecting at least one potential idiotype secreting clone having a tumor identifying region with the identical or substantially similar sequence (e.g., greater than about 80% sequence identity) as the most abundant sequence present in the tumor cell sample read.

48. The method of embodiment 1, wherein the selecting step of (l) comprises selecting at least as many potential idiotype secreting clones having a tumor identifying region with the identical or substantially similar sequence (e.g., greater than about 80% sequence identity) to as many tumor cell sample read sequences that are required to cover, e.g., greater than about 10% of the tumor cell read sequences.

49. The method of embodiment 48, wherein the tumor cell sample read sequences that are required to cover about 10% of the tumor cell sample read sequences comprise the most abundant tumor cell sample read sequences.

50. The method of embodiment 1, further comprising monitoring the clonality of the B-cell derived malignancy, wherein said monitoring comprises:

(n) obtaining isolated nucleic acid from another cell sample of one or more cells of the B-cell derived malignancy in the subject taken from the subject at a time subsequent to that of the cell sample of (a) of embodiment 1;

(o) repeating steps (b)-(l) of embodiment 1 on the isolated nucleic acid of (n);

(p) determining the abundance of the tumor identifying region sequences in amplicons in the sample of (n) that are similar or substantially similar to (e.g., greater than about 80% sequence identity) the tumor identifying region sequence(s) contained in the selected clone(s) used to produce the idiotype vaccine selected in step (l) of embodiment 1;

(q) determining the abundance of the tumor identifying region sequences in amplicons in the sample of (n) that were present in the tumor cell sample amplicon but were not contained in the idiotype vaccine prepared in step (m) of embodiment 1; and (r) determining the abundance of the tumor identifying region sequences in amplicons in the sample of (n) that are similar or substantially similar to (e.g., greater than about 80% sequence similarity) the tumor identifying region sequence(s) contained in the selected clone(s) of step (l) and used to produce the idiotype vaccine of step (m) but which harbor one or more nucleotide differences in the tumor identifying region ("tumor identifying region mutants").

51. The method of embodiment 50, further comprising preparing an updated idiotype vaccine for treatment of the B-cell derived malignancy in the subject, wherein the updated vaccine comprises an idiotype immunoglobulin which is selected to contain one or more of the following:

(a) the tumor identifying regions sequence(s) contained in the tumor identifying region mutants;

(b) the tumor identifying region sequence(s) not present in the original tumor cell sample of (a) of embodiment 1 but present in the subsequent cell sample of (n) of embodiment 50;

(c) one or more of the tumor identifying region sequence(s) contained in a prior idiotype vaccine.

52. The method of embodiment 1, wherein the tumor identifying region comprises a rearranged VDJ region of the immunoglobulin heavy chain (IgH) gene, and wherein said method further comprises monitoring the clonality of the B-cell derived malignancy, wherein said monitoring comprises:

(n) obtaining isolated nucleic acid from another cell sample of one or more cells of the B-cell derived malignancy in the subject taken from the subject at a time subsequent to that of the cell sample of (a) of embodiment 1;

(o) repeating steps (b)-(l) of embodiment 1 on the isolated nucleic acid of (n);

(p) determining the abundance of the rearranged VDJ region sequences in amplicons in the sample of (n) that are similar or substantially similar to (e.g., greater than about 80% sequence identity) the rearranged VDJ region sequence(s) contained in the selected clone(s) used to produce the idiotype vaccine selected in step (l) of embodiment 1;

(q) determining the abundance of the tumor identifying region sequences in amplicons in the sample of (n) that were present in the tumor cell sample amplicon but were not contained in the idiotype vaccine prepared in step (m) of embodiment 1; and (r) determining the abundance of the rearranged VDJ region sequences in amplicons in the sample of (n) that are similar or substantially similar to (e.g., greater than about 80% sequence similarity) the rearranged VDJ region sequence(s) contained in the selected clone(s) of step (l) and used to produce the idiotype vaccine of step (m) but which harbor one or more nucleotide differences in the complementary determining region 3 (CDR3) ("CDR3 mutants").

53. The method of embodiment 52, further comprising preparing an updated idiotype vaccine for treatment of the B-cell derived malignancy in the subject, wherein the updated vaccine comprises an idiotype immunoglobulin which is selected to contain one or more of the following:

(a) the rearranged VDJ region sequence(s) contained in the CDR3 mutants;

(b) the rearranged VDJ region sequence(s) not present in the original tumor cell sample of (a) of embodiment 1 but present in the subsequent cell sample of (n) of embodiment 50;

(c) one or more of the rearranged VDJ region sequence(s) contained in a prior idiotype vaccine.

54. The method of embodiment 51, wherein preparing the updated vaccine further comprises conjugating the selected idiotype immunoglobulin with an immunogenic carrier molecule.

55. The method of embodiment 54, wherein the immunogenic carrier molecule comprises keyhole limpet hemocyanin (KLH).

56. The method of embodiment 51, further comprising administering the updated vaccine to the subject.

57. The method of embodiment 56, further comprising administering an effective amount of an adjuvant to the subject.

58. The method of embodiment 57, wherein the adjuvant comprises granulocyte monocyte-colony stimulating factor (GM-CSF).

59. A method for selecting an idiotype vaccine for treatment of a B-cell derived malignancy in a subject, comprising (a) sequencing amplicons that collectively span a portion of the genomic region of one or more cells that is characteristic of a B-cell malignancy tumor cell sample (the "tumor identifying region"), resulting in reads (the "tumor cell sample reads") that are a quantity of sequences representative of the nucleic acid sequences of the tumor identifying region present in the tumor cell sample;

(b) aligning the tumor cell sample reads to reference sequences;

(c) producing a plurality of clones from the tumor cell sample ("potential idiotype-secreting clones"), wherein each clone is representative of one clonal population of B-cells harboring the tumor identifying region common to one clonal population of B-cells;

(d) isolating nucleic acid from one or more of the potential idiotype-secreting clones ("potential idiotype secreting clones nucleic acid sample");

(e) amplifying at least a portion of the tumor identifying region of the potential idiotype secreting clones nucleic acid sample, resulting in amplicons that collectively span the tumor identifying region ("the potential idiotype secreting clone amplicon pool");

(f) sequencing the amplicons of the potential idiotype secreting clone amplicon pool, wherein the resulting reads ("potential idiotype secreting clone reads") are a quantity of sequences representative of the nucleic acid sequences of the tumor identifying region present in the tumor cell sample;

(g) optionally, aligning the tumor cell sample reads to reference sequences (an alternative comprises aligning VDJ from tumor to VDJ from tumor cell sample (e.g., biopsy) with a suitable threshold, e.g., greater than about 80% sequence identity);

(h) determining a quantity of each sequence read from the tumor cell sample reads;

(i) aligning the potential idiotype secreting clone reads with the most abundant tumor cell sample reads (the number of unique sequences which comprise e.g., greater than about 10% of the tumor cell sample reads); and (j) selecting one or more potential idiotype secreting clones from the plurality of potential idiotype secreting clones, wherein the selected clone(s) has the same or substantially similar tumor identifying region (>80% sequence identity) as the most abundant tumor cell sample reads.

60. The method of embodiment 59, further comprising: (k) preparing an idiotype vaccine for treatment of the B-cell derived malignancy, wherein the vaccine comprises an idiotype immunoglobulin from the selected clone(s) having the same or substantially similar tumor identifying region as the most abundant tumor cell sample reads.

61. The method of embodiment 60, further comprising (l) administering the idiotype vaccine to the subject.

62. A method for selecting an idiotype vaccine for treatment of a B-cell derived malignancy in a subject, comprising:

(a) sequencing amplicons of a potential idiotype secreting clone amplicon pool, wherein the resulting reads ("potential idiotype secreting clone reads") are a quantity of sequences representative of the nucleic acid sequences of a tumor identifying region present in a cell sample of the malignancy ("tumor cell sample"), wherein the tumor identifying region comprises a portion of the genomic region of one or more cells of the malignancy that is characteristic of the tumor cell sample, and wherein the potential idiotype secreting clone amplicon pool comprises amplicons that collectively span the tumor identifying region;

(b) aligning tumor cell sample reads to reference sequences, wherein the tumor cell sample reads are sequences of amplicons that collectively span the tumor identifying region;

(c) determining a quantity of each sequence read from the tumor cell sample reads;

(d) aligning the potential idiotype secreting clone reads with the most abundant tumor cell sample reads (the number of unique sequences which comprise e.g., greater than about 10% of the tumor cell sample reads); and (e) selecting one or more potential idiotype secreting clones from the plurality of potential idiotype secreting clones, wherein the selected clone(s) has the same or substantially similar tumor identifying region (e.g., greater than about 80% sequence identity; however, other thresholds may be used) as the most abundant tumor cell sample reads.

63. The method of embodiment 62, further comprising: (f) preparing an idiotype vaccine for treatment of the B-cell derived malignancy, wherein the vaccine comprises an idiotype immunoglobulin from the selected clone(s) having the same or substantially similar tumor identifying region as the most abundant tumor cell sample reads.

64. The method of embodiment 63, further comprising (g) administering the idiotype vaccine to the subject.

65. A method for producing an idiotype vaccine for treatment of a B-cell derived malignancy in a subject, comprising (a) aligning potential idiotype secreting clone reads with tumor cell sample reads that are determined to be the most abundant (the number of unique sequences which comprise e.g., greater than about 10% of the tumor cell sample reads), wherein the tumor cell sample reads are sequences of amplicons that collectively span a tumor identifying region, wherein the tumor identifying region comprises a portion of the genomic region of one or more cells of the malignancy that is characteristic of a tumor cell sample of the malignancy, and wherein the potential idiotype secreting clone reads are a quantity of sequences representative of the nucleic acid sequences of the tumor identifying region present in the tumor cell sample of the malignancy;

(b) selecting one or more potential idiotype secreting clones from the plurality of potential idiotype secreting clones, wherein the selected clone(s) has the same or substantially similar tumor identifying region (>80% sequence identity) as the most abundant tumor cell sample reads; and (c) preparing an idiotype vaccine for treatment of the B-cell derived malignancy, wherein the vaccine comprises an idiotype immunoglobulin from the selected clone(s) having the same or substantially similar tumor identifying region as the most abundant tumor cell sample reads.

66. An idiotype vaccine prepared by the method of any one of the preceding embodiments.

67. A method for treating a B-cell derived malignancy in a subject, comprising administering an effective amount of an idiotype vaccine prepared by the method of any one of the preceding embodiments.

68. The method of any preceding embodiment, wherein the potential idiotype-secreting clones are produced by hybridoma rescue fusion hybridization in the same bioreactor (e.g., hollow fiber bioreactor) or wherein each potential idiotype-secreting clone is produced in a separate bioreactor (e.g., hollow fiber bioreactor) from other potential idiotype-secreting clones.

Following are examples which illustrate procedures for practicing the invention. These examples should not be construed as limiting. All percentages are by weight and all solvent mixture proportions are by volume unless otherwise noted.

Figure 3A:
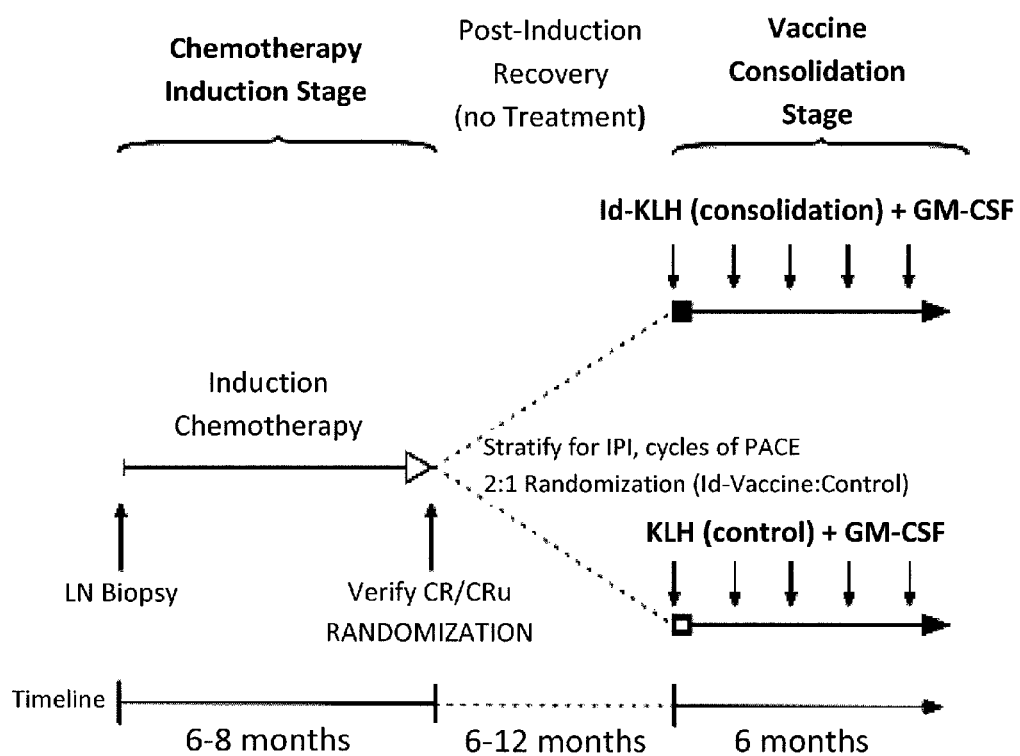
FIGS. 3A and 3B are, respectively, a clinical trial schema and flow chart of enrollment, randomization, and treatment.
Figure 3B:
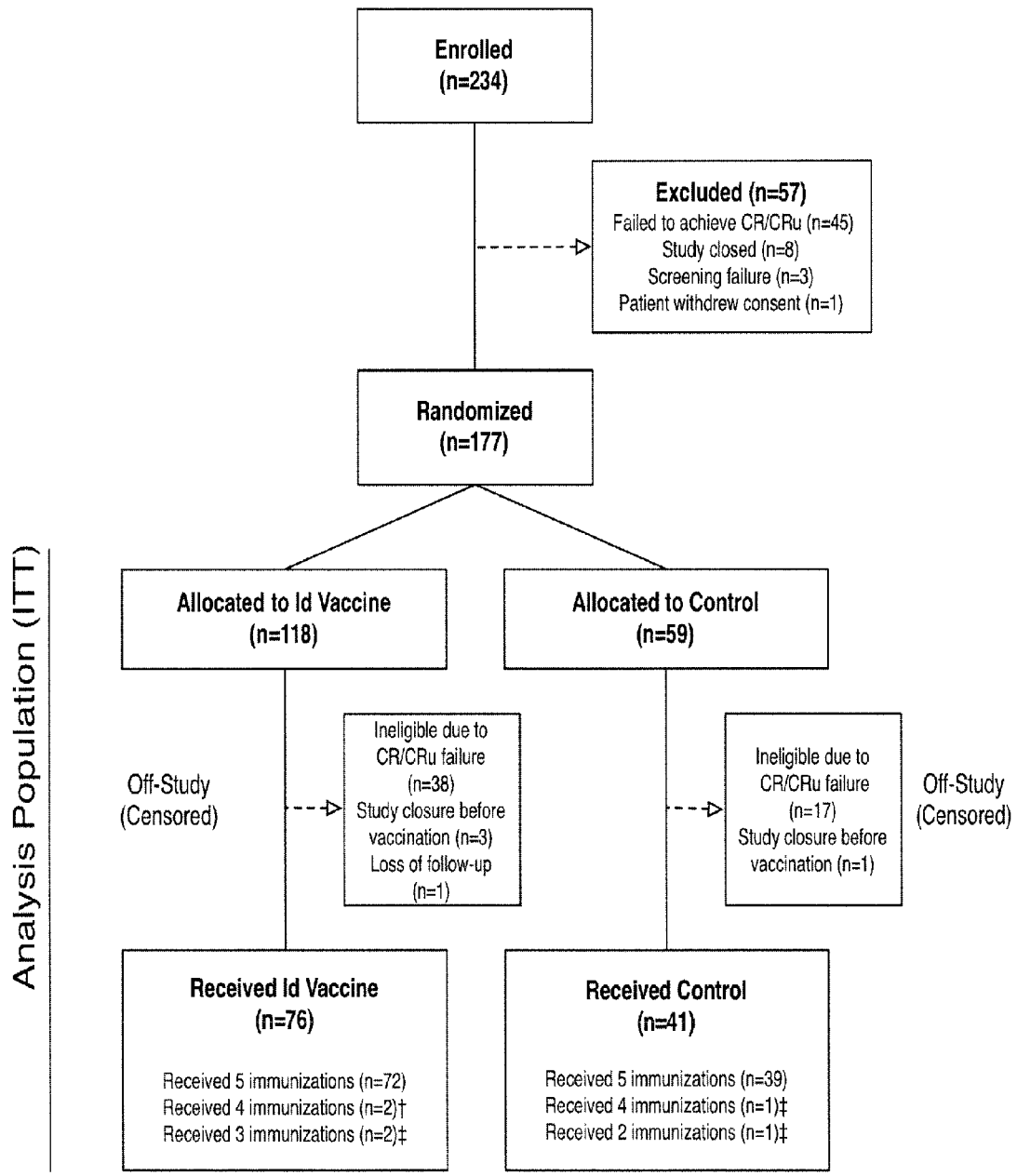
Figure 4:
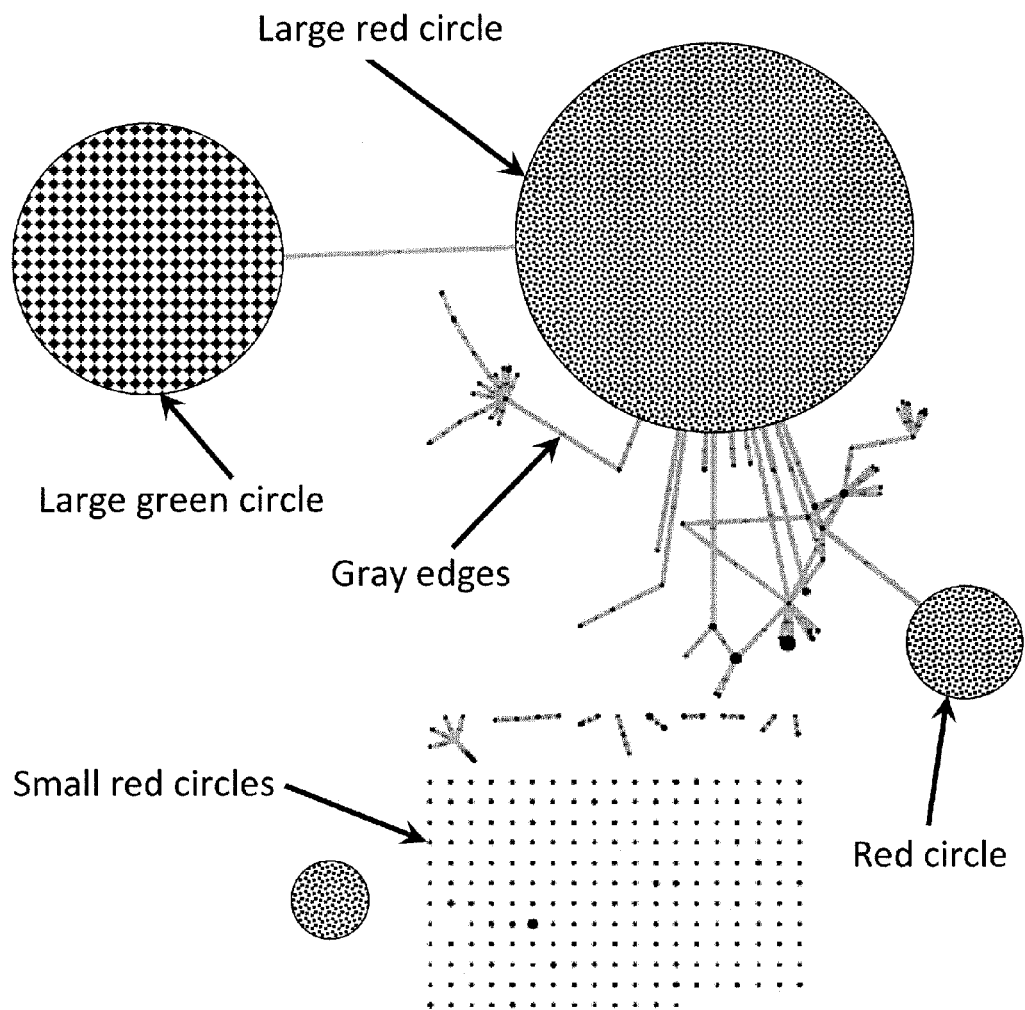
FIG. 4 shows plots used to visualize B-cell clonality in the tumor samples of Example 1, where each point or node represents a cluster of DNA sequences with high inter-sequence identity (VDJ gene rearrangement), and each line between nodes represents highly matched tumor and tumor-derived hybridoma idiotype sequences. (Green) Hybridoma sequence (clustered around sequence ID HP17LVG01D3X04; large green circle) matches (gray edges) the predominant tumor sequence group (HP17LVG01B1C99; large red circle). In contrast, the hybridoma did not match numerous other B-cell sequences (small red circles) present in the tumor biopsy (red circles).

Example 1—Immunoprofiling of B-Cell Repertoire in Tumor Biopsies and Hybridoma-Derived Vaccines 76 patients with advanced-stage follicular lymphoma in first complete remission were vaccinated with hybridoma-derived idiotype vaccine. This involved generating patient-specific tumor-derived cell lines which secreted tumor-derived immunoglobulin as the antigen, which was then conjugated to an immune adjuvant KLH and co-administered to the patents with GM-CSF (see FIGS. 2, 3A, and 3B).

The control arm was 41 patients with advanced-stage FL in first remission treated with KLH and GM-CSF. Vaccination improved disease-free survival (DFS) by a median of 13.6 months, and is the first vaccine of its kind to show these results in a clinical trial.

Due to the vaccine's hybridoma-rescue fusion production process, the inventors suspected that they capture substantial tumor heterogeneity in the production cell lines, and subsequently, the vaccine can indeed be thought of as a "multivalent" immunotherapy that targets numerous tumor clones simultaneously.

The inventors subsequently had four patient biopsies and matching end-of-production hybridoma cell lines, along with pre- and post-vaccination blood samples sequenced using Roche 454 emPCR sequencing. The first set of data indicates the presence of several thousand unique amplicons of the IgH CDR2 BCRs from this biopsy and the matching hybridoma blood samples.

Boyd S D et al. conducted massively parallel 454 sequencing of patient samples and the resulting analysis showed very detailed views of various hematologic malignancies, including FL and CLL (Boyd S D et al., "Measurement and clinical monitoring of human lymphocyte clonality by massively parallel V-D-J pyrosequencing," 2009, Sci Transmed, 1(12):1-8). With samples from the cancer patients, they obtained disease-specific signatures of clonal B-cell proliferation events. The present inventors have extended this approach to immunoprofile the B-cell repertoire in biopsies along with hybridoma-derived vaccine, and the clinical outcomes with stored blood samples at various time points. Using these methods, it is possible to track, for the first time, a tumor's composition, with its matched immunotherapy, and the T-cell immune response via emPCR DNA sequencing.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for selecting an idiotype vaccine for treatment of a B-cell derived malignancy in a subject, comprising:

(a) obtaining isolated nucleic acid from a cell sample comprising one or more cells of the B-cell derived malignancy (the "tumor cell sample");

(b) amplifying at least a portion of the genomic region of the one or more cells that is characteristic of the tumor cell sample (the "tumor identifying region"), resulting in amplicons that collectively span the tumor identifying region (the "tumor cell sample amplicons");

(c) sequencing the tumor cell sample amplicons, resulting in reads (the "tumor cell sample reads") that are a quantity of sequences representative of the nucleic acid sequences of the tumor identifying region present in the tumor cell sample;

(d) producing a plurality of clones from the tumor cell sample ("potential idiotype-secreting clones"), wherein each clone is representative of one clonal population of B-cells harboring the tumor identifying region common to one clonal population of B-cells;

(e) isolating nucleic acid from one or more of the potential idiotype-secreting clones ("potential idiotype secreting clones nucleic acid sample");
(f) amplifying at least a portion of the tumor identifying region of the potential idiotype secreting clones nucleic acid sample, resulting in amplicons that collectively span the tumor identifying region ("the potential idiotype secreting clone amplicon pool");
(g) sequencing the amplicons of the potential idiotype secreting clone amplicon pool, wherein the resulting reads ("potential idiotype secreting clone reads") are a quantity of sequences representative of the nucleic acid sequences of the tumor identifying region present in the tumor cell sample;
(h) determining a quantity of each sequence read from the tumor cell sample reads;
(i) aligning the potential idiotype secreting clone reads with the most abundant tumor cell sample reads; and
(j) selecting one or more potential idiotype secreting clones from the plurality of potential idiotype secreting clones, wherein the selected clone(s) has the same or substantially similar tumor identifying region as the most abundant tumor cell sample reads.

2. The method of claim 1, further comprising: (k) preparing an idiotype vaccine for treatment of the B-cell derived malignancy, wherein the vaccine comprises an idiotype immunoglobulin from the selected clone(s) having the same or substantially similar tumor identifying region as the most abundant tumor cell sample reads.

3. The method of claim 2, wherein preparing the idiotype vaccine further comprises conjugating the idiotype immunoglobulin with an immunogenic carrier molecule.

4. The method of claim 1, wherein the tumor identifying region of step (b) comprises complementarity determining region 3 (CDR3) of the immunoglobulin heavy chain (IgH) gene.

5. The method of claim 1, wherein the tumor identifying region of step (b) comprises:
(a) a rearranged VDJ region of the immunoglobulin heavy chain (IgH) gene; or
(b) a rearranged VJ region of the immunoglobulin kappa (IgK) gene; or
(c) a rearranged VJ region of the immunoglobulin lambda (IgL) gene.

6. The method of claim 1, wherein the tumor identifying region of step (b) is a translocation region associated with the B-cell derived malignancy.

7. The method of claim 6, wherein the translocation region comprises:
(a) a bcl-1/IgH fusion sequence, wherein the B-cell derived malignancy is mantle cell lymphoma (MCL); or
(b) a bcl-2/IgH fusion sequence, wherein the B-cell derived malignancy is follicular lymphoma; or
(c) a bcl-3/IgH fusion sequence, wherein the B-cell derived malignancy is B-cell chronic lymphocytic leukemia (CLL); or
(d) a bcl-6/IgH fusion sequence, wherein the B-cell derived malignancy is diffuse large cell lymphoma (DLCL); or
(e) a fibroblast growth factor receptor (FGFR)/IgH fusion sequence, wherein the B-cell derived malignancy is multiple myeloma; or
(f) a cyclin D1 sequence, wherein the B-cell derived malignancy is multiple myeloma; or
(g) a c-myc/IgH fusion sequence, wherein the B-cell derived malignancy is Burkitt's lymphoma; or
(h) a bcl-6/IgL fusion sequence, wherein the B-cell derived malignancy is diffuse large cell lymphoma (DLCL); or
(i) a bcl-6 or CD95 fusion sequence; wherein the B-cell derived malignancy is Non-Hodgkin's lymphoma (NHL); or
(j) a Pax-5, c-myc, Pim-1, or Rho/TTF sequence; wherein the B-cell derived malignancy is DLCL; or
(k) a bcl-6, Pax-5, c-myc, Pim-1, Rho/TTF sequence; wherein the B-cell derived malignancy is NHL.

8. The method of claim 1, wherein the tumor identifying region comprises a unique genetic element.

9. The method of claim 8, wherein the unique genetic element is selected from among a translocation, single nucleotide polymorphism (SNP), or somatic mutation.

10. The method of claim 8, wherein the method further comprises sequencing the nucleic acid of the tumor sample entirely using whole genome sequencing or exome sequencing; and aligning the determined nucleic acid sequences with reference sequences to identify the unique genetic elements of the one or more cells of the tumor cell sample.

11. The method of claim 1, wherein the tumor identifying region of step (b) comprises a rearranged VDJ region of the immunoglobulin heavy chain (IgH) gene, and wherein said amplifying of step (b) comprises amplifying DNA between primers that target the framework region (FR1, FR2, and/or FR3) and joining (J) region of the IgH variable gene of the one or more cells.

12. The method of claim 1, wherein the sequencing step of (c) comprises high-throughput sequencing (HTS).

13. The method of claim 1, further comprising performing a quality control step on the potential idiotype secreting clone reads of (g).

14. The method of claim 13, wherein the quality control step comprises: eliminating any potential idiotype secreting clone reads of (g) that are the result of sequence artifact; and/or assigning a quality score to each potential idiotype secreting clone read of (g), comparing each assigned quality score to a reference threshold quality score, and replacing or annotating any nucleotides in each potential idiotype secreting clone amplicon designated not to have achieved the threshold quality score.

15. The method of claim 2, further comprising monitoring the clonality of the B-cell derived malignancy, wherein said monitoring comprises:
(l) obtaining isolated nucleic acid from another cell sample of one or more cells of the B-cell derived malignancy in the subject taken from the subject at a time subsequent to that of the cell sample of (a);
(m) repeating steps (b)-(j) on the isolated nucleic acid of (l);
(n) determining the abundance of the tumor identifying region sequences in amplicons in the sample of (l) that are similar or substantially similar to the tumor identifying region sequence(s) contained in the selected clone(s) used to produce the idiotype vaccine selected in step (j);
(o) determining the abundance of the tumor identifying region sequences in amplicons in the sample of (l) that were present in the tumor cell sample amplicon but were not contained in the idiotype vaccine prepared in step (k); and
(p) determining the abundance of the tumor identifying region sequences in amplicons in the sample of (l) that are similar or substantially similar to the tumor identifying region sequence(s) contained in the selected clone(s) of step (j) and used to produce the idiotype vaccine of step (k) but which harbor one or more nucleotide differences in the tumor identifying region ("tumor identifying region mutants").

16. The method of claim 15, further comprising preparing an updated idiotype vaccine for treatment of the B-cell derived malignancy in the subject, wherein the updated vaccine comprises an idiotype immunoglobulin which is selected to contain one or more of the following:
    (a) the tumor identifying regions sequence(s) contained in the tumor identifying region mutants;
    (b) the tumor identifying region sequence(s) not present in the original tumor cell sample of (a) but present in the subsequent cell sample of (l), of claim 15;
    (c) one or more of the tumor identifying region sequence(s) contained in a prior idiotype vaccine.

17. The method of claim 2, wherein the tumor identifying region comprises a rearranged VDJ region of the immunoglobulin heavy chain (IgH) gene, and wherein said method further comprises monitoring the clonality of the B-cell derived malignancy, wherein said monitoring comprises:
    (l) obtaining isolated nucleic acid from another cell sample of one or more cells of the B-cell derived malignancy in the subject taken from the subject at a time subsequent to that of the cell sample of (a);
    (m) repeating steps (b)-(j) on the isolated nucleic acid of (l);
    (n) determining the abundance of the rearranged VDJ region sequences in amplicons in the sample of (l) that are similar or substantially similar to the rearranged VDJ region sequence(s) contained in the selected clone(s) used to produce the idiotype vaccine selected in step (j);
    (o) determining the abundance of the tumor identifying region sequences in amplicons in the sample of (n) that were present in the tumor cell sample amplicon but were not contained in the idiotype vaccine prepared in step (m); and
    (p) determining the abundance of the rearranged VDJ region sequences in amplicons in the sample of (l) that are similar or substantially similar to the rearranged VDJ region sequence(s) contained in the selected clone(s) of step (j) and used to produce the idiotype vaccine of step (m) but which harbor one or more nucleotide differences in the complementary determining region 3 (CDR3) ("CDR3 mutants").

18. The method of claim 17, further comprising preparing an updated idiotype vaccine for treatment of the B-cell derived malignancy in the subject, wherein the updated vaccine comprises an idiotype immunoglobulin which is selected to contain one or more of the following:
    (a) the rearranged VDJ region sequence(s) contained in the CDR3 mutants;
    (b) the rearranged VDJ region sequence(s) not present in the original tumor cell sample of (a) but present in the subsequent cell sample of (n);
    (c) one or more of the rearranged VDJ region sequence(s) contained in a prior idiotype vaccine.

19. A method for selecting an idiotype vaccine for treatment of a B-cell derived malignancy in a subject, comprising:
    (a) sequencing amplicons that collectively span a portion of the genomic region of one or more cells that is characteristic of a B-cell malignancy tumor cell sample (the "tumor identifying region"), resulting in reads (the "tumor cell sample reads") that are a quantity of sequences representative of the nucleic acid sequences of the tumor identifying region present in the tumor cell sample;
    (b) aligning the tumor cell sample reads to reference sequences;
    (c) producing a plurality of clones from the tumor cell sample ("potential idiotype-secreting clones"), wherein each clone is representative of one clonal population of B-cells harboring the tumor identifying region common to one clonal population of B-cells;
    (d) isolating nucleic acid from one or more of the potential idiotype-secreting clones ("potential idiotype secreting clones nucleic acid sample");
    (e) amplifying at least a portion of the tumor identifying region of the potential idiotype secreting clones nucleic acid sample, resulting in amplicons that collectively span the tumor identifying region ("the potential idiotype secreting clone amplicon pool");
    (f) sequencing the amplicons of the potential idiotype secreting clone amplicon pool, wherein the resulting reads ("potential idiotype secreting clone reads") are a quantity of sequences representative of the nucleic acid sequences of the tumor identifying region present in the tumor cell sample;
    (g) determining a quantity of each sequence read from the tumor cell sample reads;
    (h) aligning the potential idiotype secreting clone reads with the most abundant tumor cell sample reads; and
    (i) selecting one or more potential idiotype secreting clones from the plurality of potential idiotype secreting clones, wherein the selected clone(s) has the same or substantially similar tumor identifying region as the most abundant tumor cell sample reads.

20. The method of claim 19, further comprising: (j) preparing an idiotype vaccine for treatment of the B-cell derived malignancy, wherein the vaccine comprises an idiotype immunoglobulin from the selected clone(s) having the same or substantially similar tumor identifying region as the most abundant tumor cell sample reads.

21. The method of claim 20, further comprising (k) administering the idiotype vaccine to the subject.

22. A method for treating a B-cell derived malignancy in a subject, comprising administering an effective amount of an idiotype vaccine prepared by the method of claim 1.

23. The method of claim 1, wherein the potential idiotype-secreting clones are produced by hybridoma rescue fusion hybridization in the same bioreactor or wherein each potential idiotype-secreting clone is produced in a separate bioreactor from other potential idiotype-secreting clones.

24. The method of claim 22, wherein the B-cell derived malignancy is in complete remission at the time of said administering.

25. The method of claim 1, further comprising, after (c) and before (d), aligning the tumor cell sample reads to reference sequences, or to the potential idiotype-secreting clones if using VDJ spanning primers.

26. The method of claim 1, further comprising, after (g) and before (h), aligning the tumor cell sample reads to reference sequences.

* * * * *